(12) United States Patent
Leung et al.

(10) Patent No.: US 11,975,181 B2
(45) Date of Patent: May 7, 2024

(54) POLYMERIC INJECTION SYSTEMS

(71) Applicant: CREDENCE MEDSYSTEMS, INC., Menlo Park, CA (US)

(72) Inventors: Mina M. Leung, Mountain View, CA (US); Jeff Tillack, Foster City, CA (US); Stephen H. Diaz, Palo Alto, CA (US); Alan E. Shluzas, San Carlos, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 737 days.

(21) Appl. No.: 16/837,835

(22) Filed: Apr. 1, 2020

(65) Prior Publication Data
US 2020/0306462 A1 Oct. 1, 2020

Related U.S. Application Data

(60) Provisional application No. 62/827,767, filed on Apr. 1, 2019.

(51) Int. Cl.
*A61M 5/32* (2006.01)
*A61M 5/31* (2006.01)
(Continued)

(52) U.S. Cl.
CPC ........ *A61M 5/3293* (2013.01); *A61M 5/3134* (2013.01); *A61M 5/3148* (2013.01);
(Continued)

(58) Field of Classification Search
CPC .. A61M 2005/3131; A61M 2005/3208; A61M 2207/10; A61M 5/3134;
(Continued)

(56) References Cited

U.S. PATENT DOCUMENTS 6,224,588 B1 * 5/2001 Jentzen ................. A61M 39/10
604/533
2009/0163859 A1 6/2009 Lloyd et al.
(Continued)

FOREIGN PATENT DOCUMENTS

| GB | 2464112 | 4/2010 |
| GB | 2466883 | 7/2010 |
| WO | WO 2010/099145 | 9/2010 |

OTHER PUBLICATIONS

PCT International Search Report and Written Opinion for International Appln. No. PCT/US2020/026230, Applicant Credence Medsystems, Inc., dated Jul. 2, 2020 (12 pages).
(Continued)

*Primary Examiner* — Shefali D Patel
(74) *Attorney, Agent, or Firm* — Vista IP Law Group LLP

(57) ABSTRACT

An injection system includes a molded body member having a body connection member at a distal end of the molded body member. The system also includes a needle hub assembly coupled to the distal end of the molded body member. The needle hub assembly includes a needle hub coupled to the body connection member of the molded body member, a needle coupled to the needle hub, and a barbed band disposed around a proximal end of the needle hub and having a barb. The barbed band allows rotation of the needle hub assembly relative to the body connection member in a first direction, while preventing rotation of the needle hub assembly relative to the body connection member in a second direction.

10 Claims, 22 Drawing Sheets

(51) Int. Cl.
  *A61M 5/34* (2006.01)
  *C08L 53/00* (2006.01)
(52) U.S. Cl.
  CPC ..... *A61M 5/347* (2013.01); *A61M 2005/3131* (2013.01); *A61M 2005/3208* (2013.01); *A61M 2207/10* (2013.01); *C08L 53/00* (2013.01)
(58) Field of Classification Search
  CPC .... A61M 5/3148; A61M 5/3293; A61M 5/34; A61M 5/344; A61M 5/347; A61M 2005/3142; A61M 2005/5006; A61M 5/345; A61M 39/1011; A61M 2039/1033; A61M 2039/1038; C08L 53/00
  See application file for complete search history.

(56) References Cited

U.S. PATENT DOCUMENTS

| | | | |
|---|---|---|---|
| 2016/0206834 A1* | 7/2016 | Shluzas | A61M 5/346 |
| 2017/0224933 A1 | 8/2017 | Hagihira et al. | |
| 2018/0126068 A1 | 5/2018 | Nazzaro et al. | |

OTHER PUBLICATIONS

Foreign OA to JP Patent Appln. No. 2021-558647 dated Feb. 20, 2024 (with English translation).
Foreign OA to IN Patent Appln. No. 202147046996 dated Feb. 21, 2024 (with English translation).

* cited by examiner

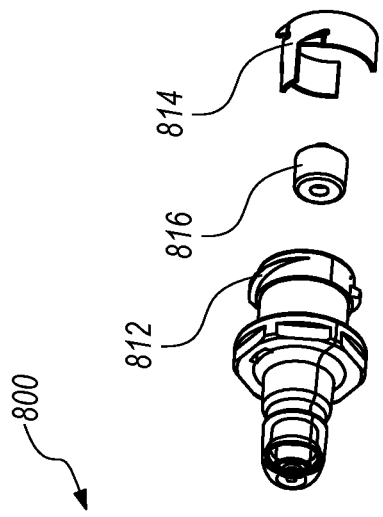
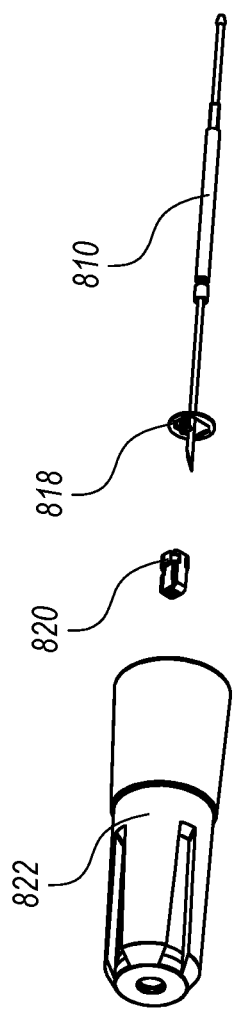
FIG. 9
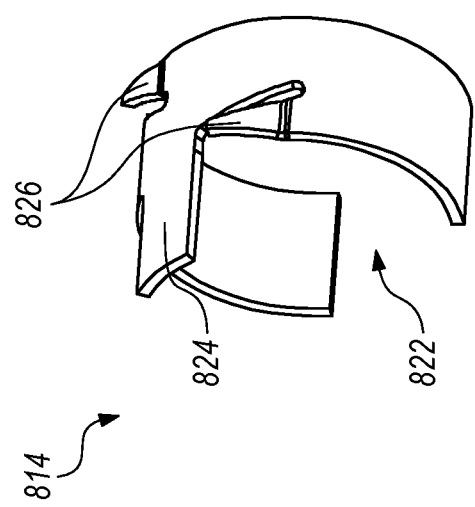
FIG. 10

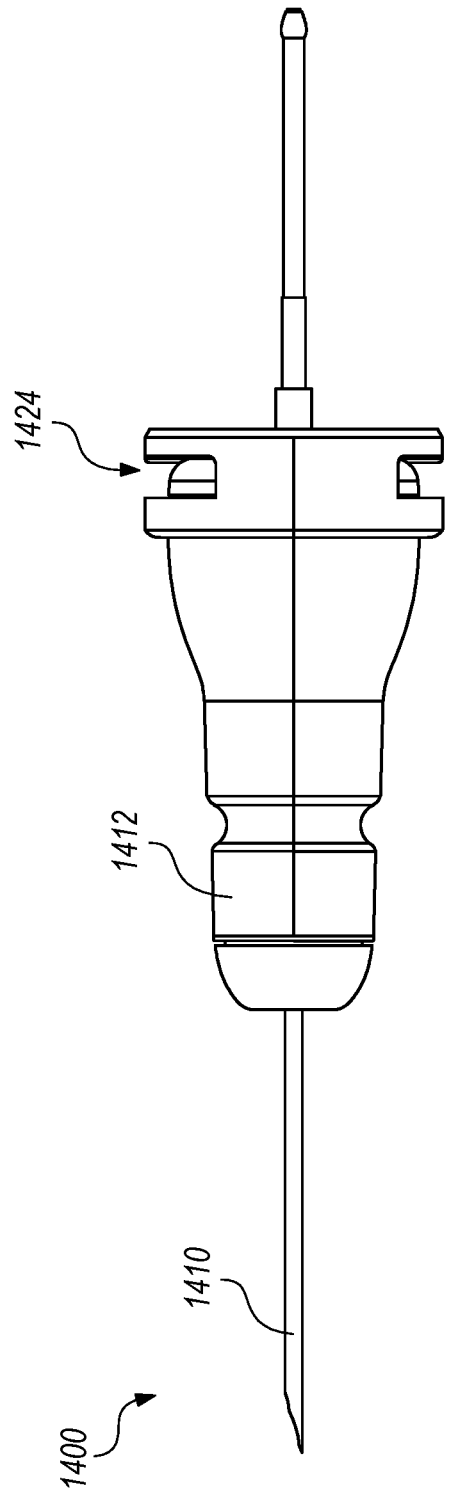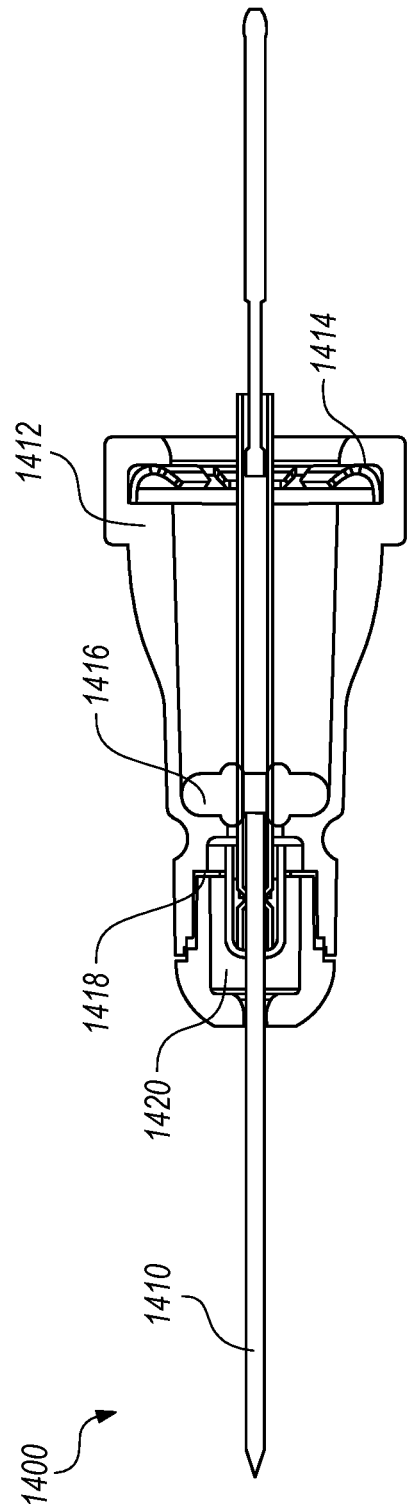

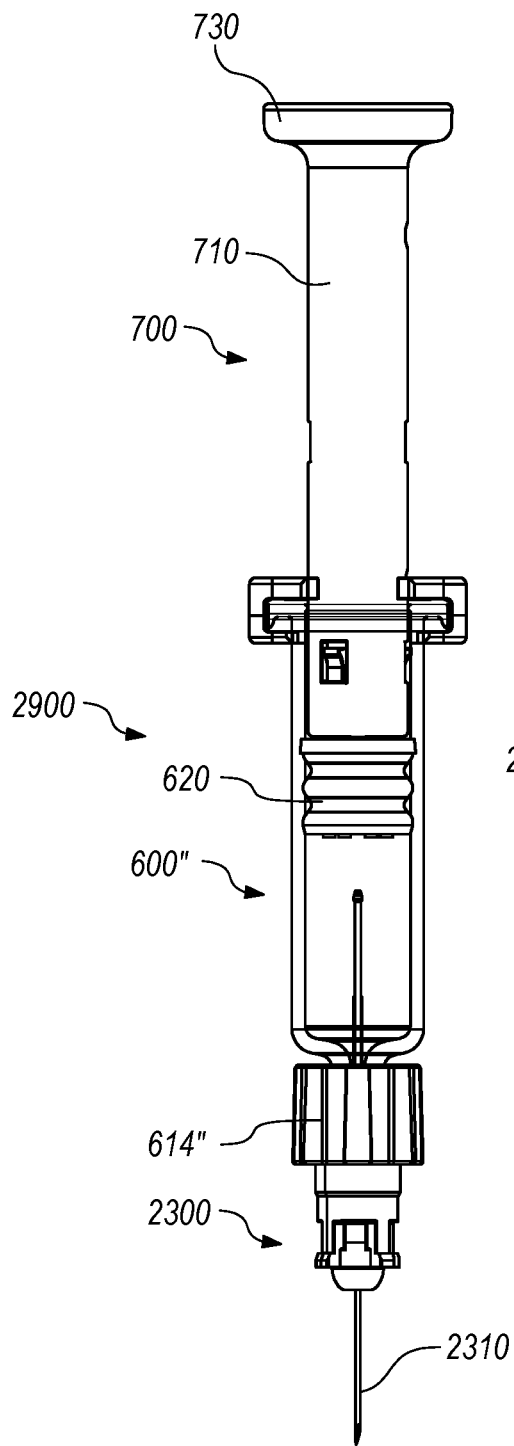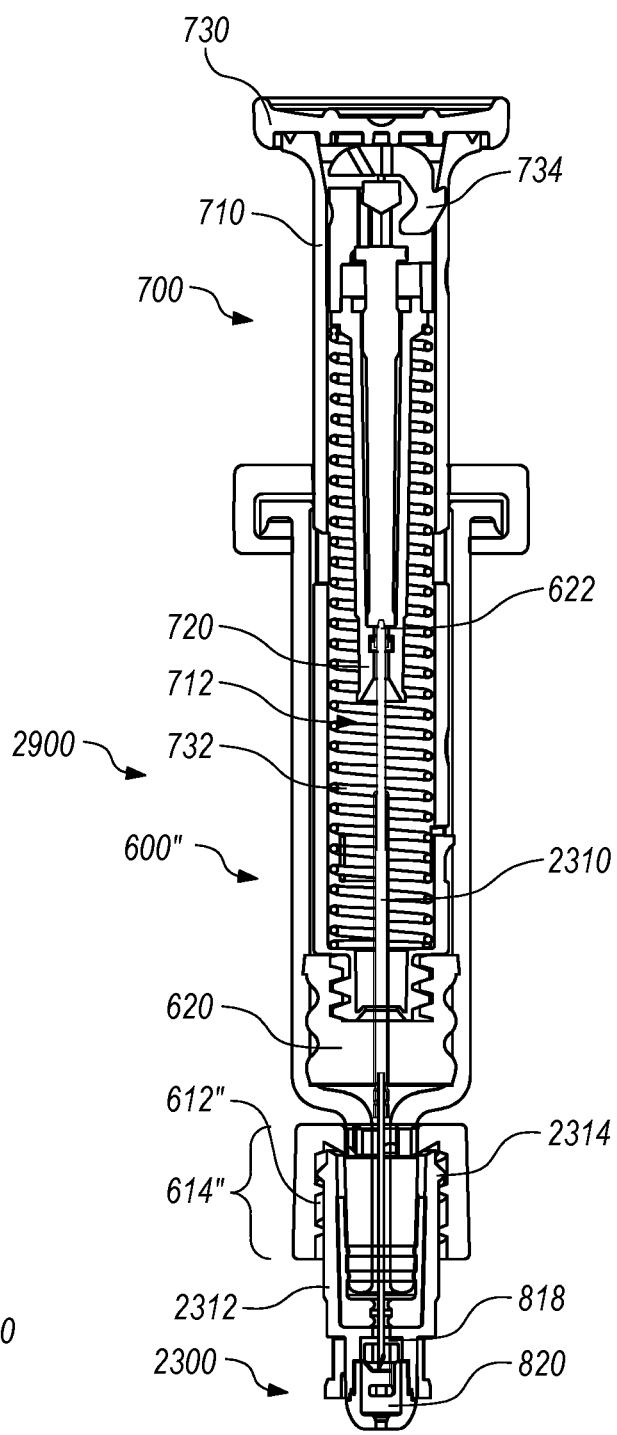
*FIG. 29A*  *FIG. 29B*

POLYMERIC INJECTION SYSTEMS

The present application claims priority to (1) U.S. Provisional Patent Application Ser. No. 62/827,767, filed on Apr. 1, 2019, entitled "POLYMERIC INJECTION SYSTEMS." This application includes subject matter similar to the subject matter described in the following co-owned U.S. patent applications: (2) U.S. Utility patent application Ser. No. 14/696,342, filed Apr. 24, 2015 entitled "SYSTEM AND METHOD FOR SAFETY SYRINGE"; (3) U.S. Utility patent application Ser. No. 14/543,787, filed Nov. 17, 2014 entitled "SYSTEM AND METHOD FOR DRUG DELIVERY WITH A SAFETY SYRINGE"; and (4) U.S. Utility patent application Ser. No. 14/321,706, filed Jul. 1, 2014 entitled "SAFETY SYRINGE." The contents of the above-mentioned applications are fully incorporated herein by reference as though set forth in full.

FIELD OF THE INVENTION

The present invention relates generally to injection systems and devices, and more particularly to injection systems and devices related to injection in healthcare environments. Even more particularly, the present invention relates to injection systems and devices including molded polymeric injection system bodies, and methods for manufacturing and assembling same.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three luer-type syringes (12) are depicted, each having a luer fitting geometry (14) disposed distally, so that they may be coupled with other devices having similar mating geometry, such as the luer manifold assembly (16) depicted in FIG. 2B. The luer manifold assembly of FIG. 2B may be used to administer liquid drugs to the patient intravenously with or without the use of an intravenous infusion bag. The luer fittings (14) of the syringes of FIG. 2A may be termed the "male" luer fittings, while those of FIG. 2B (18) may be termed the "female" luer fittings; one of the luer interfaces may be threaded (in which case the configuration may be referred to as a "luer lock" configuration) so that the two sides may be coupled by relative rotation, which may be combined with compressive loading. In other words, in one luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a luer engagement using compression without threads or rotation (such a configuration may be referred to as a "slip-on" or "conical" luer configuration). While such luer couplings are perceived to be relatively safe for operators, there is risk of medicine spilling/leaking and parts breakage during the loading to provide a luer coupling.

The use of needle injection configurations, on the other hand, carries with it the risk of a sharp needle contacting or poking a person or structure that is not desired. For this reason, so called "safety syringes" have been developed. One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety. Other "safety syringes" are described in U.S. patent application Ser. Nos. 14/696,342, 14/543,787, 14/321,706, 62/416,102, 62/431,382, and 62/480,276, the contents of which are fully incorporated herein by reference as though set forth in full.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a luer type interface (FIG. 5A shows the cap 35 in place; FIG. 5B has the cap removed to illustrate the luer interface (14). Liquid medicine may reside in the volume, or medicine reservoir, (40) between the distal seal (35) and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body (34) structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the medicine chamber or reservoir (40), and to assist with expulsion of the associated fluid through the needle, a plunger tip (36) may be positioned within the syringe body (34). The syringe body may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as the system (41) featured in FIG. 5C, which attempts to meet all of the standards, or at least a portion thereof, with one solution by including most or all parts needed to perform an injection (body, stopper, needle, plunger, etc.) As a result of trying to meet these standards for many different scenarios, such products may have significant limitations (including some of those described above in reference to FIGS. 3-4B) and relatively high inventory and utilization expenses.

Some injection system bodies are formed by molding polymers such as Cyclic Olefin Copolymer ("COC") or Cyclic Olefin Polymer ("COP") or other polymers suitable for injection molding, blow molding or other manufacturing processes. Molding injection system bodies is a cost-effective and high throughput method of manufacturing injection system components with an acceptable error rate. For instance, FIG. 6 shows a molded polymer syringe body 600 including an integral luer connector 610 and an inwardly facing thread 612 to facilitate coupling of a needle hub assembly (not shown; see e.g., FIG. 8) onto the molded polymer syringe body 600. The luer connector 610, the inwardly facing thread 612, and the distal end of the syringe body 600 having the inwardly facing thread 612 together form a needle coupling assembly/luer nut 614. The integrated needle coupling assembly/luer nut 614 eliminates the step of attaching a luer nut to the distal end of a syringe body.

In other embodiments, an injection system body (e.g., syringe or cartridge body) may be constructed from a polymer with an inert coating disposed on a surface, preferably an interior surface, of the injection system body. The inert coating is configured to separate the liquid medicine from the polymer of the injection system body. Examples of the inert coating material include, but are not limited to: silica-based coatings (e.g., silicon dioxide, glass, borosilicate glass, hydrophobic organosiloxane) and other polymer materials configured to be non-reactive with the medicine inside the injection system body. The inert coating may be placed on an interior surface of the injection system body using processes such as plasma vapor deposition, chemical adhesives, and/or other adhesive or mechanical methods. The inert coating material may also be configured to reduce the rate of gas transmission (e.g., of oxygen, nitrogen, or other gasses) through the injection system body during storage with the injection system pre-filled with medicine. The inert coating may also provide a lubricious surface to reduce the static and/or dynamic friction of the stopper sliding inside the injection system body. The lubricious surface may be configured to reduce or eliminate the need to apply silicone oil on interior surfaces of the injection system body. The inert coating may also reduce the amount of leachable or extractable chemicals transferred from a polymer injection system body into the medicine contained within the medicine chamber of the polymer injection system body during storage. The inert coating may also reduce changes in the pH of the medicine contained within the medicine chamber of the injection system body during storage.

FIG. 7 depicts the distal end of the molded polymer syringe body 600 shown in FIG. 6 in greater detail. FIG. 7 illustrates two problems with currently available molded polymer syringe bodies. First, the inwardly facing threads 612 on the molded polymer syringe body 600 are smooth to facilitate removal of the mold core (not shown) by unscrewing the mold core from the formed syringe body 600. The smoothness of the inwardly facing thread 612 reduces the amount of interference available to couple a needle hub assembly (not shown) onto the molded polymer syringe body 600. In effect, if the inwardly facing thread 612 are smooth enough to allow inadvertent unscrewing/removal of the mold core (not shown) after molding, then the inwardly facing thread 612 will also allow inadvertent removal of the needle hub assembly and any other connector coupled to the molded polymer syringe body 600. Such inadvertent unscrewing/removal may occur during shipping, use, etc.

FIG. 7 also illustrates that the opening 616 at the distal end of the luer connector 612 has a limited minimum size due to the mold forming process. The opening 616 of the molded polymer syringe body 600 in FIG. 7 has a minimum diameter of about 2 mm (0.079 in.), which is more than twice the diameter of the approximately 1 mm (0.036 in.) needle/tube (not shown; see e.g., FIG. 8). As a result, the needle is not well centered in the luer connector 610 or the molded polymer syringe body 600. Significant deviation from a center position (misalignment) can interfere with the interaction of the needle/tube with other injection system components, such as the needle retraction components described in U.S. patent application Ser. Nos. 14/696,342, 14/543,787, 14/321,706, 62/416,102, 62/431,382, and 62/480,276, the contents of which have been previously Incorporated by reference herein. While FIGS. 6 and 7 depict a molded polymer syringe body 600, the mechanisms for preventing removal of a needle hub assembly from a molded body member can also be used with molded polymer cartridges according to various embodiments. Additionally, the mechanisms for preventing removal of a needle hub from an injection system body may also be employed in the injection systems including an injection molded threaded luer interface/needle coupling assembly affixed to the distal end of a glass injection system body (e.g., syringe).

There is a need for injection system components for use with molded polymer injection system bodies that address the shortcomings of currently-available configurations. In particular, there is a need for needle hub assemblies with anti-removal/retention mechanisms configured to more securely couple the needle hub assemblies to molded polymer injection system bodies. Further, there is a need for injection system components that center needle/tubes in the molded polymer injection system bodies and their distal connectors to minimize opportunities for system error due to misalignment. Addressing these and other limitations of molded polymer injection system bodies allows these cost-effective and easy to manufacture system bodies to be incorporated into more injection systems.

SUMMARY

Embodiments are directed to injection systems. In particular, the embodiments are directed to injection system components for use with molded polymeric injection system bodies.

In one embodiment, an injection system includes a molded body member having a body connection member at a distal end thereof. The system also includes a needle hub assembly coupled to the distal end of the injection system body. The needle hub assembly includes a needle hub coupled to the body connection member, a needle coupled to the needle hub, and a barbed band disposed around a proximal end of the needle hub and having a barb. The barbed band allows rotation of the needle hub assembly relative to the body connection member in a first direction, while preventing rotation of the needle hub assembly relative to the body connection member in a second direction.

In one or more embodiments, the system also includes a stopper member disposed in the molded body member and a plunger member coupled thereto. The needle may be configured to be retracted at least partially into the molded body member upon manipulation of the plunger member to position the stopper member at the distal end of the molded body member.

In one or more embodiments, the needle hub includes a plurality of recesses configured to facilitate rotation of the needle hub assembly relative to the body connection member. The body connection member may include a space having inward facing threads. The body connection member may include an integrated needle coupling assembly/luer nut.

In one or more embodiments, the system also includes a sealing member disposed between the distal end of the body member and an inner surface of the needle hub. The sealing member may include an inward extension configured to center the needle in the distal end of the body member. The barbed band may include a spike extending toward the second direction and biased to spring radially outward. The body member may be molded from Cyclic Olefin Copolymer or Cyclic Olefin Polymer. The body member may have an inert coating on the interior surfaces of the medicine chamber of the body member.

In another embodiment, an injection system includes a molded body member. The molded body member includes a body connection member at a distal end thereof, and a notch disposed on a distally facing surface thereof. The system also includes a needle hub assembly coupled to the distal end of the injection system body. The needle hub assembly includes a needle hub coupled to the body connection member, a needle coupled to the needle hub, and a detent disposed on a proximally facing surface of the needle hub. The detent is configured to fit in the notch and prevent preventing rotation of the needle hub assembly relative to the body connection member when the needle hub assembly is coupled to the body member.

In one or more embodiments, the system also includes a stopper member disposed in the molded body member and a plunger member coupled thereto. The needle may be configured to be retracted at least partially into the molded body member upon manipulation of the plunger member to position the stopper member at the distal end of the molded body member.

In one or more embodiments, the needle hub includes a plurality of recesses configured to facilitate rotation of the needle hub assembly relative to the body connection member. The body connection member may include a space having inward facing threads. The body connection member may include an integrated needle coupling assembly/luer nut.

In one or more embodiments, the system also includes a sealing member disposed between the distal end of the body member and an inner surface of the needle hub. The sealing member may include an inward extension configured to center the needle in the distal end of the body member. The body member may be molded from Cyclic Olefin Copolymer or Cyclic Olefin Polymer. The body member may have an inert coating on the interior surfaces of the medicine chamber of the body member.

In still another embodiment, an injection system includes a molded body member having a body connection member at a distal end thereof. The system also includes a needle hub assembly coupled to the distal end of the injection system body. The needle hub assembly includes a needle hub coupled to the body connection member, a needle coupled to the needle hub, and a retention ring disposed around a proximal end of the needle hub and having a plurality of teeth. The retention ring allows proximal movement of the needle hub assembly relative to the body connection member, while preventing distal movement of the needle hub assembly relative to the body connection member.

In one or more embodiments, the system also includes a stopper member disposed in the molded body member and a plunger member coupled thereto. The needle may be configured to be retracted at least partially into the molded body member upon manipulation of the plunger member to position the stopper member at the distal end of the molded body member.

In yet another embodiment, an injection system includes a molded body member having a body connection member at a distal end thereof. The system also includes a needle hub assembly coupled to the distal end of the injection system body. The needle hub assembly includes a needle hub coupled to the body connection member, a needle coupled to the needle hub, and a braking tab disposed on an outer surface of the needle hub assembly and in contact with an inner surface of the body connection member. The braking tab allows rotation of the needle hub assembly relative to the body connection member in a first direction, while preventing rotation of the needle hub assembly relative to the body connection member in a second direction.

In one or more embodiments, the system also includes a stopper member disposed in the molded body member and a plunger member coupled thereto. The needle may be configured to be retracted at least partially into the molded body member upon manipulation of the plunger member to position the stopper member at the distal end of the molded body member.

The aforementioned and other embodiments of the invention are described in the Detailed Description which follows.

BRIEF DESCRIPTION OF THE DRAWINGS

The drawings described below are for illustration purposes only. The drawings are not intended to limit the scope of the present disclosure. This patent or application file contains at least one drawing executed in color. Copies of this patent or patent application publication with color drawings will be provided by the U.S. Patent and Trademark Office upon request and payment of the necessary fee.

The foregoing and other aspects of embodiments are described in further detail with reference to the accompanying drawings, in which the same elements in different figures are referred to by common reference numerals, wherein:

FIGS. 8 and 9 depict a needle hub assembly for use with a molded polymer injection system according to some embodiments.

FIG. 10 depicts anti-removal band for use in a needle hub assembly and a molded polymer injection system according to some embodiments.

FIGS. 14 to 16B depict a needle hub assembly for use with a molded polymer injection system according to some embodiments.

FIGS. 29A and 29B depict a safe injection system with a brake tab (or a locking detent) according to some embodiments.

Figure 1A:
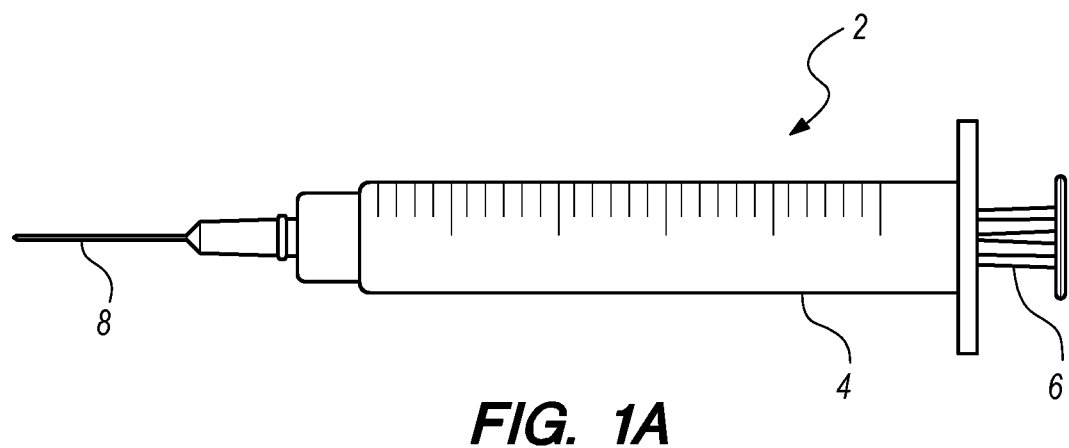
FIGS. 1A to 5C illustrate various aspects of conventional injection syringe configurations.
Figure 1B:
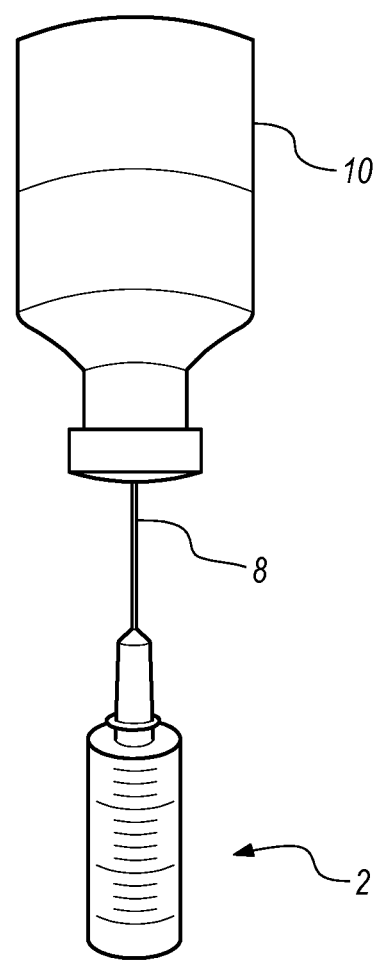
Figure 2A:
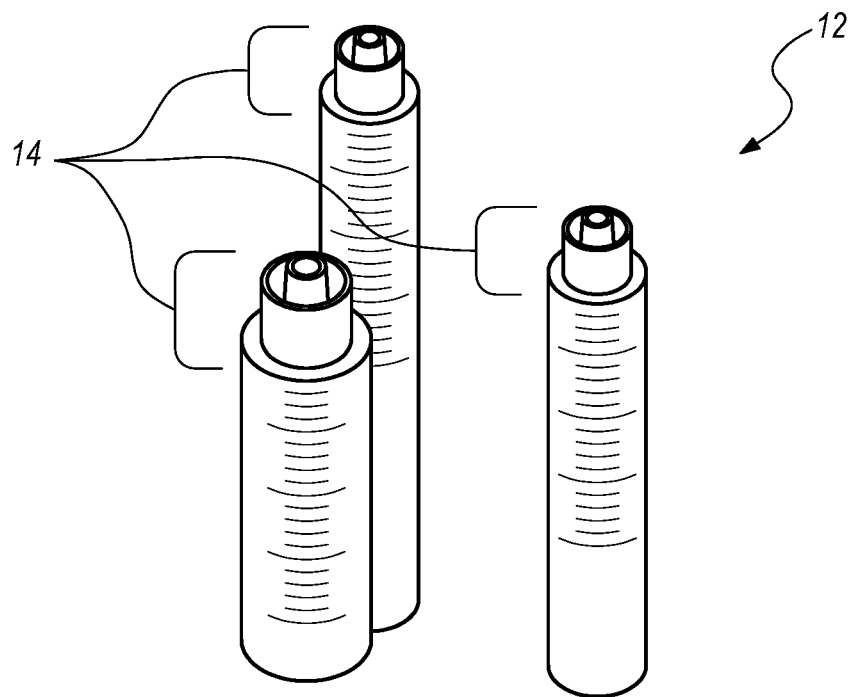
Figure 2B:
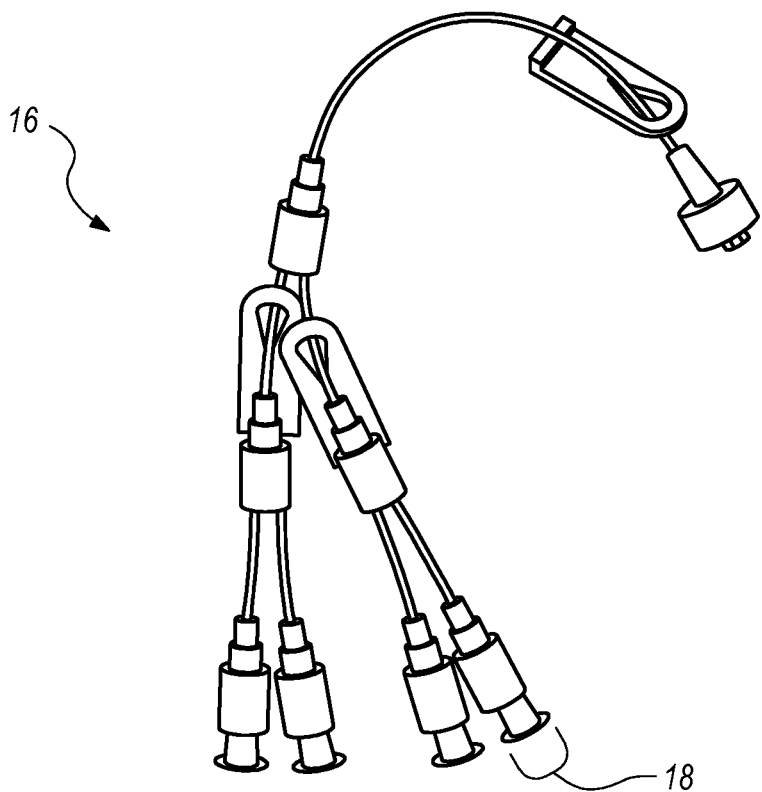
Figure 3:
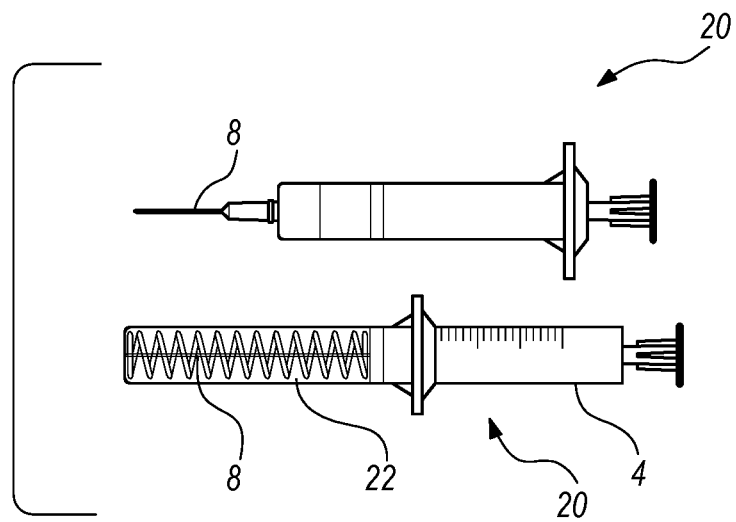
Figure 4A:
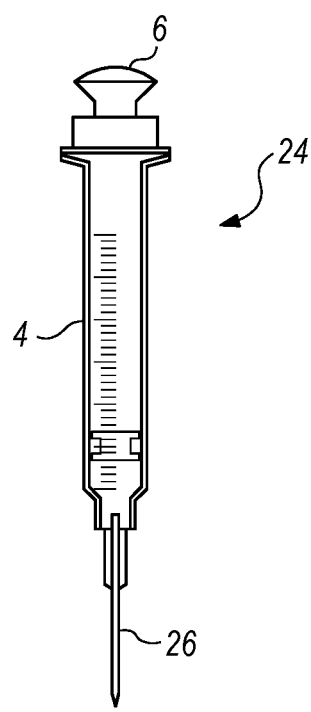
Figure 4B:
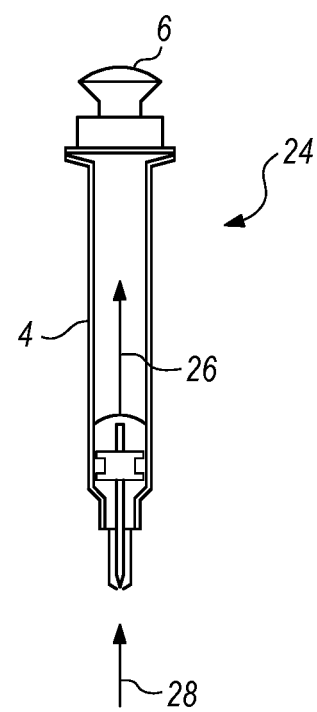
Figure 5A:
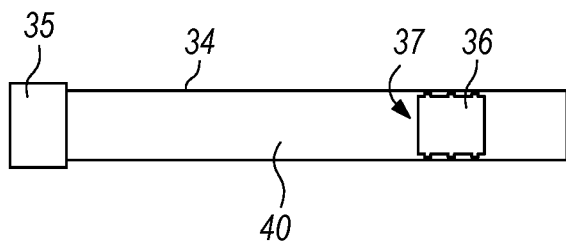
Figure 5B:
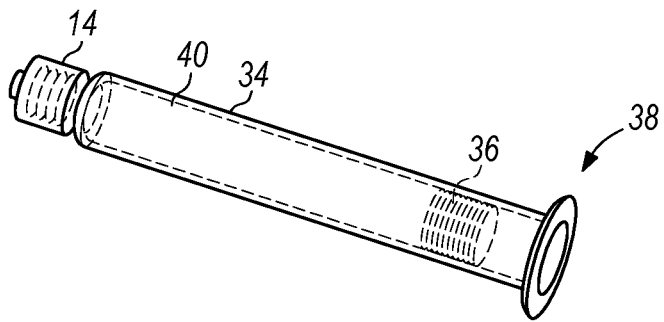
Figure 5C:
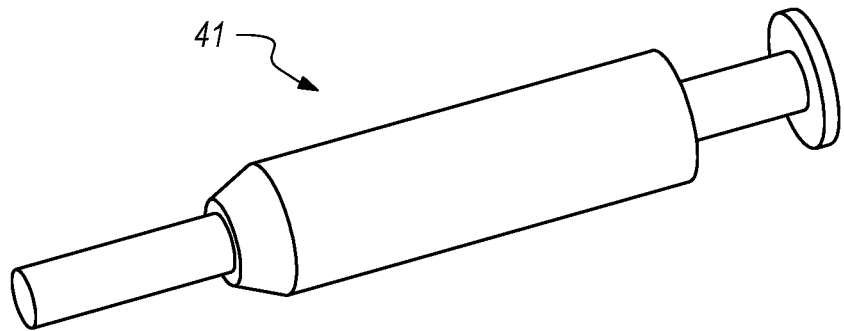

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Anti-Removal Barbed Band

Figure 8:
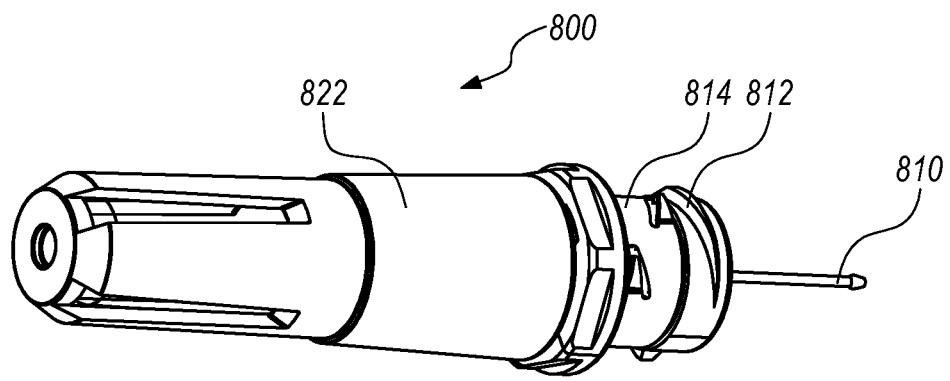

FIGS. 8 and 9 depict a needle hub assembly 800 for use with molded polymer injection system bodies according to some embodiments. The needle hub assembly 800 includes a needle 810, a threaded needle hub 812, and anti-removal band 814, a seal/guide 816, a needle latch 818, a needle latch actuator 820, and a rigid needle shield 822. The needle latch 818 and the needle latch actuator 820 are part of needle retraction systems such as those described herein and in U.S. patent application Ser. Nos. 14/696,342, 14/543,787, 14/321,706, 62/416,102, 62/431,382, and 62/480,276, the contents of which have been previously Incorporated by reference herein.

The anti-removal band 814 is depicted in detail in FIG. 10. In some embodiments, the anti-removal band 814 is made from metal to provide greater elasticity and hardness to retain the needle hub assembly 800 on a molded polymer injection system body. The hardness of the metal from which the anti-removal band 814 is formed allows the anti-removal barbs 826 thereof to dig into the softer polymer from which the injection system body 600 is made to prevent rotation of the needle hub assembly 800 relative to the injection system body 600 in the removal direction as described herein. The anti-removal band 814 is approximately 75% of a completely circular band. The opening 822 in the anti-removal band 814 allows the anti-removal band 814 to be snapped onto the needle hub 812. The anti-removal band 814 also includes a longitudinal extension 824 configured to be received in an opening in the needle hub 812 to prevent relative rotation of the anti-removal band 814 and the needle hub 812.

Still referring to FIG. 10, the anti-removal band 814 also includes a plurality (e.g., two) of anti-removal barbs 826. The anti-removal barbs 826 are pointed in a counterclockwise direction that is opposite of the clockwise direction of the inwardly facing threads in the molded polymer injection system body. Further, the distal ends of the anti-removal barbs 826 are biased to extend in a radially outward direction. As such, when the needle hub assembly 800 is threaded clockwise onto the molded polymer syringe body 600 shown in FIG. 11, the anti-removal barbs 826 do not engage the smooth walls of the molded polymer syringe body 600 adjacent to the inwardly facing threads 612. However, when the needle hub assembly 800 is rotated in the counterclockwise direction y, the anti-removal barbs 826 gouge/dig into the smooth walls of the of the molded polymer syringe body 600. This interference prevents rotation of the needle hub assembly 800 relative to the molded polymer syringe body 600 in the counterclockwise direction and removal of the needle hub assembly 800 from the molded polymer syringe body 600. The anti-removal band 814 and the anti-removal barbs 826 thereon function as a one-way clutch allowing only clockwise rotation of the needle hub assembly 800 relative to the molded polymer syringe body 600. While clockwise rotation is allowed and counterclockwise rotation is prevented in this embodiment, other embodiments may allow counterclockwise rotation and prevents clockwise rotation by modifying the direction of the anti-removal barbs 826 and the inwardly facing threads in the molded polymer injection system body.

Figure 11:
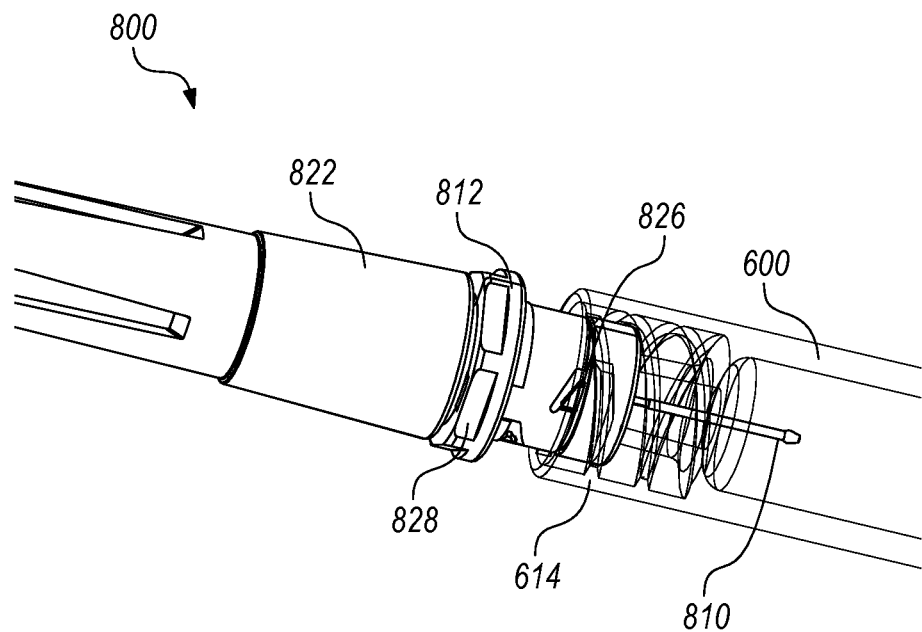
FIG. 11 depicts coupling of the needle hub assembly depicted in FIGS. 8 and 9 with the molded polymer injection system body depicted in FIGS. 6 and 7 according to some embodiments.

Still referring to FIG. 11, the needle hub 812 also includes a plurality of recesses 828 with flat surfaces. The recesses 828 on the needle hub 812 allow a wrench or socket-like device (not shown) to rotate the needle hub assembly 800 relative to the molded polymer syringe body 600. The wrench or socket-like device can be manipulated by a user or by a robot, thereby facilitating both manual and automated assembly.

Figure 12:
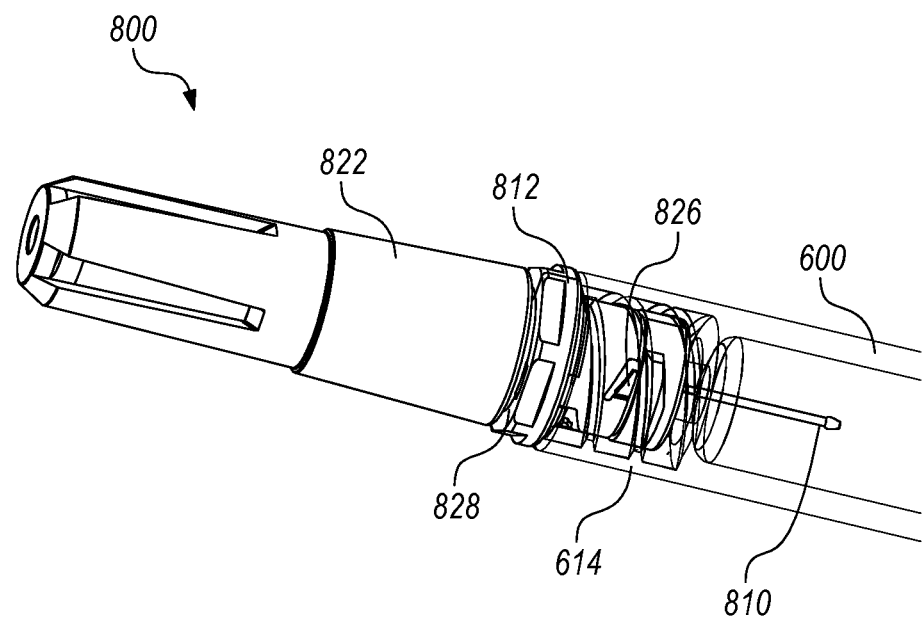
FIGS. 12 and 13 depict the needle hub assembly depicted in FIGS. 8 and 9 coupled with the molded polymer injection system body depicted in FIGS. 6 and 7 according to some embodiments.

FIG. 12 depicts the needle hub assembly 800 fully screwed onto the molded polymer syringe body 600. Due to the anti-removal barbs 826, once the needle hub assembly 800 and the molded polymer syringe body 600 are assembled, they cannot be manually separated from each other.

Figure 13:
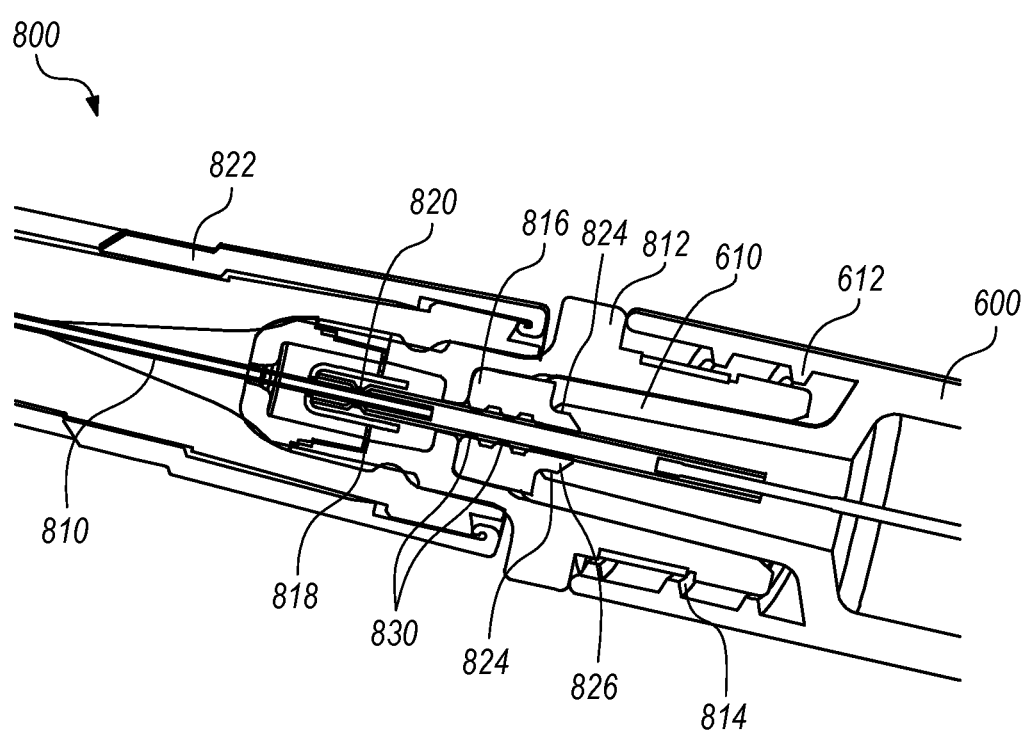

FIG. 13 depicts the needle hub assembly 800 fully screwed onto the molded polymer syringe body 600 in a cross-sectional view to show the function of the seal/guide 816. The needle/tube 810 passes through the seal/guide 616 and into the molded polymer syringe body 600. The seal/guide 816 is pressed against the distal end of the luer connector 810 by the needle hub 812, thereby sealing a distal end of the molded polymer syringe body 600 prevents fluid from exiting the distal end molded polymer syringe body 600 except through the needle/tube 810.

Further, the seal/guide 816 includes an inward extension 830 that centers the needle/tube 810 in the opening 616 at the distal end of the luer connector 612, thereby stabilizing the needle/tube 810 in the opening 616 in spite of the difference in the diameters of the needle/tube 810 and the opening 616 described above. Centering and stabilizing the needle/tube 810 in the molded polymer syringe body 600 facilitates accurate interactions between the proximal end of the needle/tube 810 and various injection system components disposed at the distal end of the molded polymer syringe body 600 as described above.

Exemplary Safe Syringe System (with Anti-Removal Barbed Band)

Figure 13A:
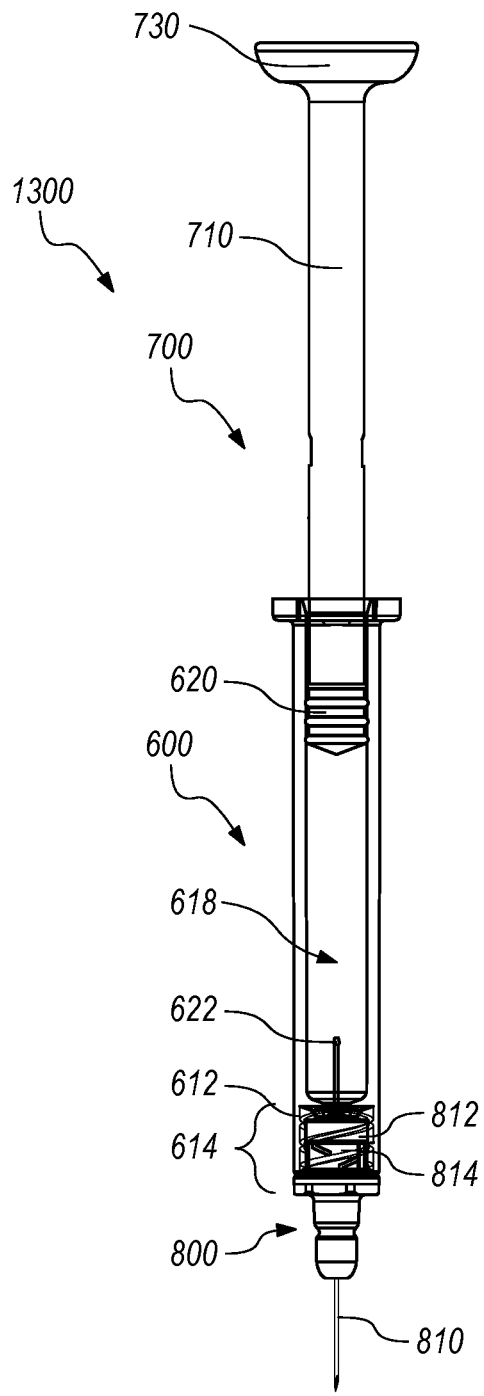
FIGS. 13A and 13B depict a safe injection system with an anti-removal barbed band according to some embodiments.
Figure 13B:
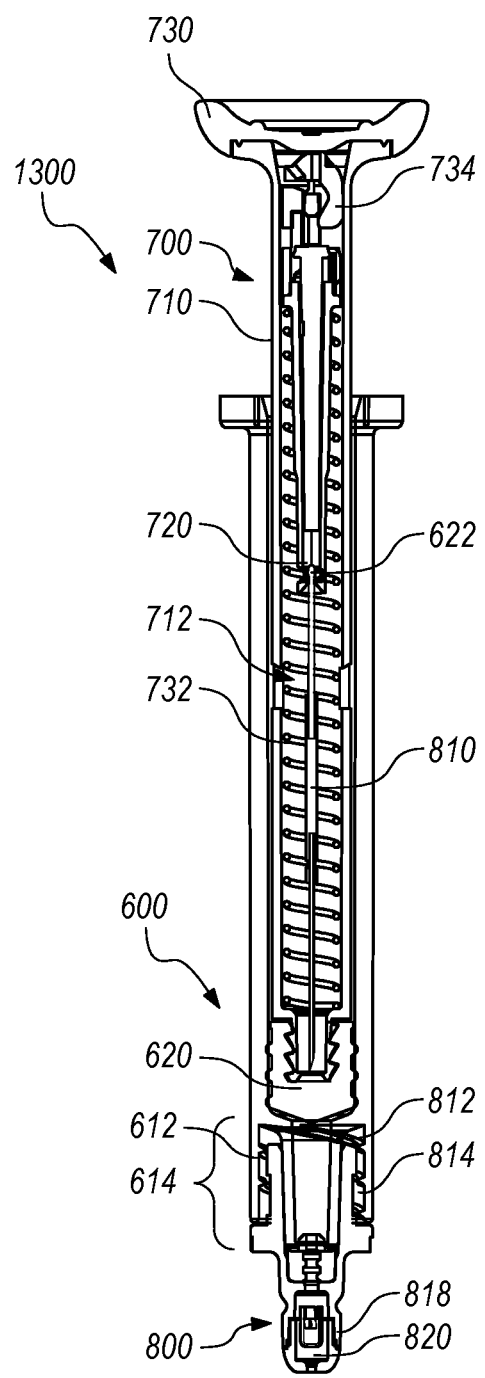
Figure 14:
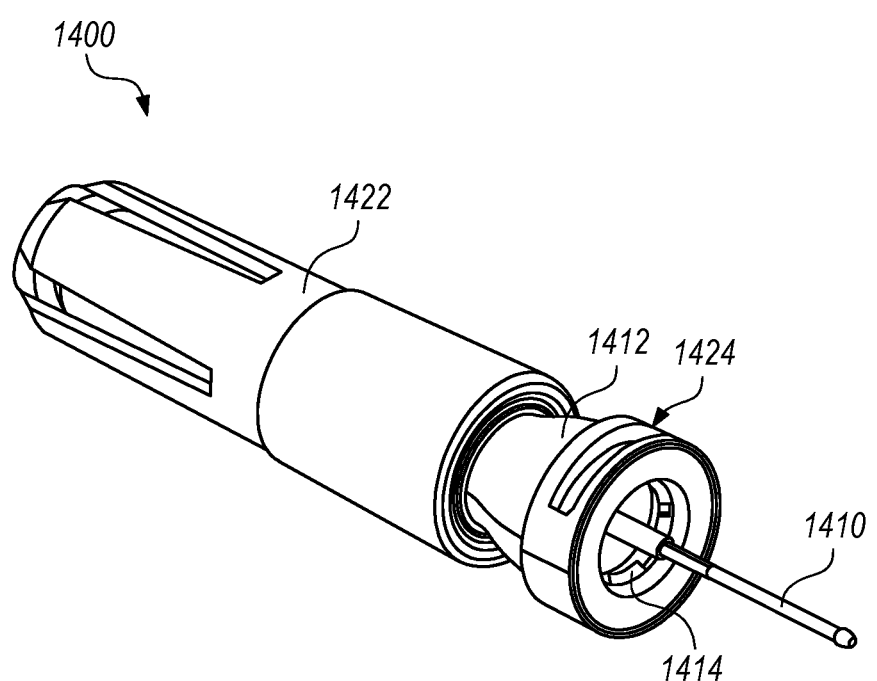

FIGS. 13A and 13B show side views of a safe injection system 1300 with an anti-removal barbed band 814 according to some embodiments. The safe injection system 1300 facilitates injection of a medicine through a needle 810 and retraction of the needle 810 into the safe injection system 1300 such that a sharp distal end of the needle is contained therein to prevent accidental needle sticks.

The safe injection system 1300 includes a molded polymeric syringe body 600 defining a medicine chamber 618, a stopper member 620 occluding the proximal end of the medicine chamber 618, and a needle coupling assembly 614 formed at the distal end of the molded polymeric syringe body 600. The medicine chamber 618 may have an inert coating on the interior surfaces thereof. The safe injection system 1300 also includes a plunger assembly 700. The plunger assembly 700 is coupled to the stopper member 620, and includes a plunger housing member 710 and a plunger manipulation interface 730.

The safe injection system 1300 further includes a needle hub assembly 800 having a needle 810 releasable coupled to a threaded needle hub 812 by a needle latch 818 as shown in FIGS. 8 and 9, and described above. The threaded needle hub 812 may be coupled to the needle coupling assembly 614 via the inwardly facing threads 612 on the needle coupling assembly 614. As shown in FIGS. 11 and 12 and described above, the barbed band 814 allows the needle hub assembly 800 to be threaded onto the needle coupling assembly 614, but prevents removal of the needle hub assembly 800 therefrom. The needle latch 818 prevents proximal movement of the needle 810 relative to the threaded needle hub 812 until the needle latch 818 is opened/released by distal movement of the needle 810. Distal movement of the needle 810 (from force applied through the stopper member 620, the plunger housing member 710, and the plunger manipulation interface 730) causes distal movement of a needle latch actuator 820 to open/release the needle latch 818.

The safe injection system 1300 controls exit of medicine from the chamber 618 distally subject to insertion of the plunger assembly 700 relative to the syringe body 600 by a user. FIG. 13A shows the safe injection system 1300 in a pre-injection configuration. With application of distally directed force onto the plunger manipulation interface 730, the plunger member 700 is moved distally relative to the molded polymeric syringe body 600, thereby expelling medicine from the chamber 618 through the needle 810 to perform an injection.

FIG. 13B shows the safe injection system 1300 in a post-injection, safe configuration. When the plunger member 700 has been manipulated distally such that the stopper member 620 is positioned near the distal end of the molded polymeric syringe body 600, a proximal end 622 of the needle 810 pierces completely through the stopper member 620 and into a plunger interior 712 defined by the plunger housing member 710. After entering the plunger interior 712 the proximal end 622 of the needle 810 is coupled to/captured by a needle retraction member 720 in the plunger assembly 700. The needle retraction member 720 is initially in a distal position (not shown) in the plunger interior 712. The needle retraction member 720 is coupled to a needle retraction spring 732. The needle retraction spring 732 is held in a compressed state by a spring latch 734, when the needle retraction member 720 is in the distal position. The needle retraction member 720, the needle retraction spring 732, and the spring latch 734 reside within the plunger interior 712.

When the stopper member 620 is positioned near the distal end of the molded polymeric syringe body 600, the needle pushes the needle latch actuator 820 distally to open/release the needle latch 818, thereby allowing proximal movement of the needle 810 relative to the needle hub assembly 800. When the stopper member 620 is reaches the distal end of the molded polymeric syringe body 600, the needle retraction member 720 actuates the spring latch 734, thereby releasing the needle retraction spring 732. Because the needle latch actuator 820 has already opened/released the needle latch 818, when the needle retraction member 720 actuates the spring latch 734, the needle retraction spring expands, thereby moving the needle retraction member 720 and the needle 810 coupled thereto into the plunger interior 712, as shown in FIG. 13B. The sharp distal tip of the needle 810 is retracted into the plunger interior 712 and the stopper member 620 to prevent accidental needle sticks after the injection is complete. In other embodiments, the sharp tip of the needle 810 is retracted to a position proximal to the distal end of the threaded needle hub 812 to prevent inadvertent needle sticks. Additional details regarding exemplary safe needle retraction mechanism are described in U.S. patent application Ser. Nos. 14/696,342, 14/543,787, 14/321,706, 62/416,102, 62/431,382, and 62/480,276, the contents of which have been previously Incorporated by reference herein.

Retaining Ring

FIGS. 14 to 16B depict a needle hub assembly 1400 for use with molded polymer injection system bodies according to some embodiments. The needle hub assembly 1400 includes a needle 1410, a needle hub 1412, and retaining ring 1414, a seal/guide 1416, a needle latch 1418, a needle latch actuator 1420, and a rigid needle shield 1422.

FIGS. 16A and 16B shows that the needle hub 1412 defines a space 1424 sized and shaped to contain the retaining ring 1414 to prevent longitudinal movement of the retaining ring 1414 and the needle hub 1412 relative to each other. FIG. 16B also shows that the seal/guide 1416 is seated at a distal end of an interior of the needle hub 1412. The needle/tube 1610 passes through the seal/guide 1616 and into a molded polymer injection system body (e.g., the molded polymer syringe body 600). The seal/guide 1416 can be pressed against the distal end of a luer connector 610 by the needle hub 1412, thereby sealing a distal end of the molded polymer syringe body 600 prevents fluid from exiting the distal end molded polymer syringe body 600 except through the needle/tube 1610.

The seal/guide also that centers the needle/tube 1610 in the opening 616 at the distal end of the luer connector 612, thereby stabilizing the needle/tube 1610 in the opening 616 in spite of the difference in the diameters of the needle/tube 1610 and the opening 616 as described above. Centering and stabilizing the needle/tube 1610 in the molded polymer syringe body 600 facilitates accurate interactions between the proximal end of the needle/tube 1610 and various injection system components disposed at the distal end of the molded polymer syringe body 600 as described above.

Figure 6:
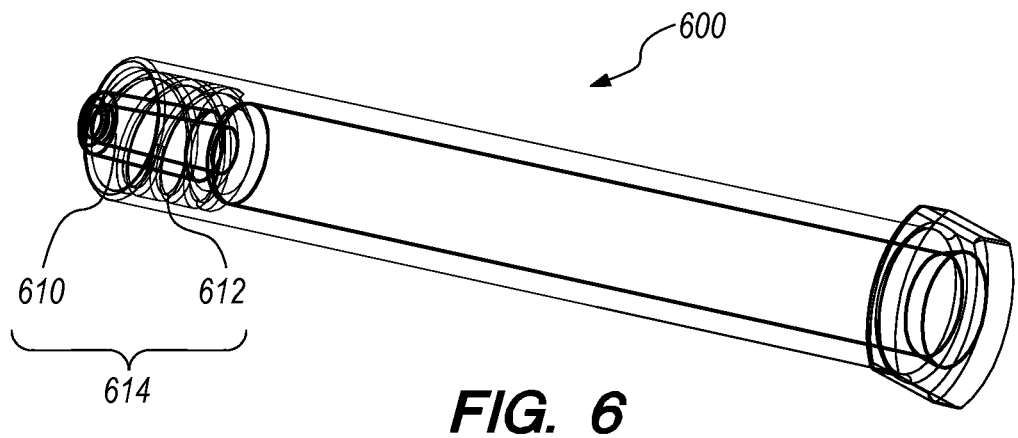
FIGS. 6 and 7 depict a molded polymer injection system body according to some embodiments.
Figure 17A:
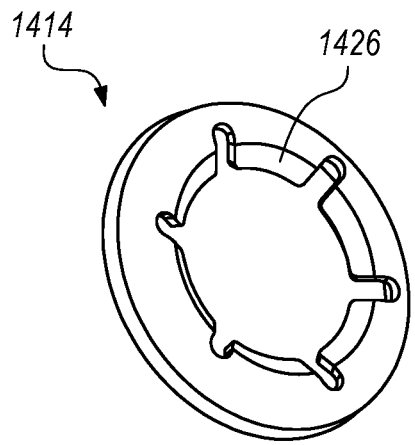
FIGS. 17A and 17B depict a retaining ring for use in a needle hub assembly and a molded polymer injection system according to some embodiments.
Figure 17B:
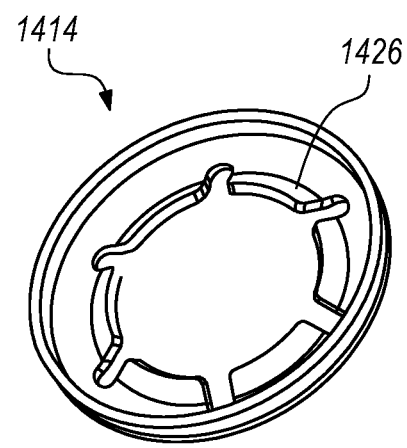

FIGS. 17A and 17B depicts a metal retaining ring 1414 for the use with a needle hub 1412 of the needle hub assembly 1400 according to some embodiments. Because the metal retaining ring 1414 includes teeth 1426 that are biased in such a way to bend more readily in one direction compared to the opposite direction, the retaining ring 1414 can slip proximally over the luer connector 610 (see FIGS. 6 and 7) more easily at the distal end of the molded polymer syringe body 600, while providing relatively more substantial resistance to removing the retaining ring 1414 distally over the luer connector 610. In fact, the teeth 1426 of the retaining ring 1414 may even gouge/dig into the luer connector 610 when the needle hub assembly 1400 is pulled away from the molded polymer syringe body 600.

There is a self-braking action that occurs between the teeth 1426 and the molded polymer syringe body 600 that helps resist the removal of the retaining ring 1414 over the luer connector 610. The teeth 1426 tend to bind harder to the luer connector 610 as more removal force is applied. This is due to the non-shallow angle that is formed between the teeth 1426 and the luer connector 610 after assembly, which increases friction between the teeth 1426 and the luer connector 610 with increasing removal force, thereby preventing the teeth 1426 from releasing the luer connector 610. The domed curvature of the teeth 1426 and the surrounding metal of the retaining ring 1414 lend structural strength to the teeth 1426, which thereby squeeze the luer connector 610 with substantial radial force, and help to reinforce the self-braking action and help the teeth 1426 to resist releasing the luer connector 610. Because the needle hub 1412 defines a space 1424 in which the retaining ring 1414 is disposed and because the molded polymer syringe body 600 include a luer connector 610 configured to interact with the retaining ring 1414, interference between the luer connector 610 and the retaining ring 1414 allows the needle hub 1412 to be mounted onto the molded polymer syringe body 600 in the proximal direction while preventing removal of the needle hub 1412 from the molded polymer syringe body 600 in the distal direction. The metal retaining ring 1414 has greater hardness and elasticity compared to the molded polymer syringe body 600 due to its metallic composition.

Figure 18:
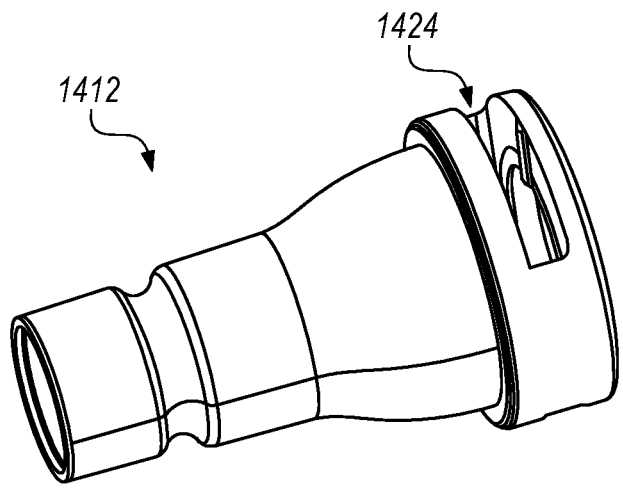
FIGS. 18 to 19B depict a needle hub for use with a retaining ring in a needle hub assembly and a molded polymer injection system according to some embodiments.
Figure 19A:
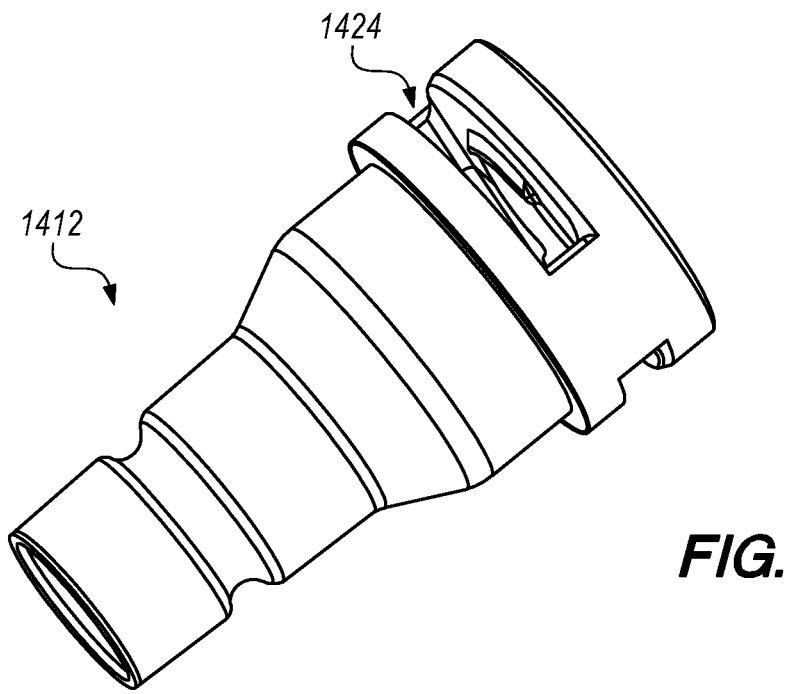
FIGS. 19C to 19E depict a safe injection system with a retaining ring according to some embodiments.
Figure 19B:
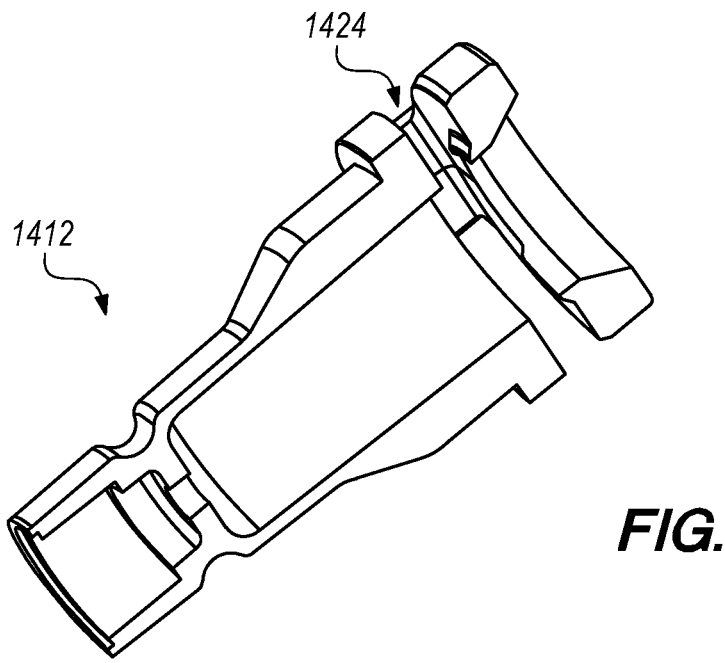

FIGS. 18 to 19B depict the needle hub 1412 with the other components omitted for clarity. As shown in FIG. 19B, the needle hub 1412 defines a space 1424 sized and shaped to contain the retaining ring 1414 to prevent longitudinal movement of the retaining ring 1414 and the needle hub 1412 relative to each other. Therefore, when the retaining ring 1414 is coupled to the molded polymer syringe body 600, the needle hub 1412 and the needle hub assembly 1400 are also coupled to the molded polymer syringe body 600.

Exemplary Safe Syringe System (with Retaining Ring)

Figure 19C:
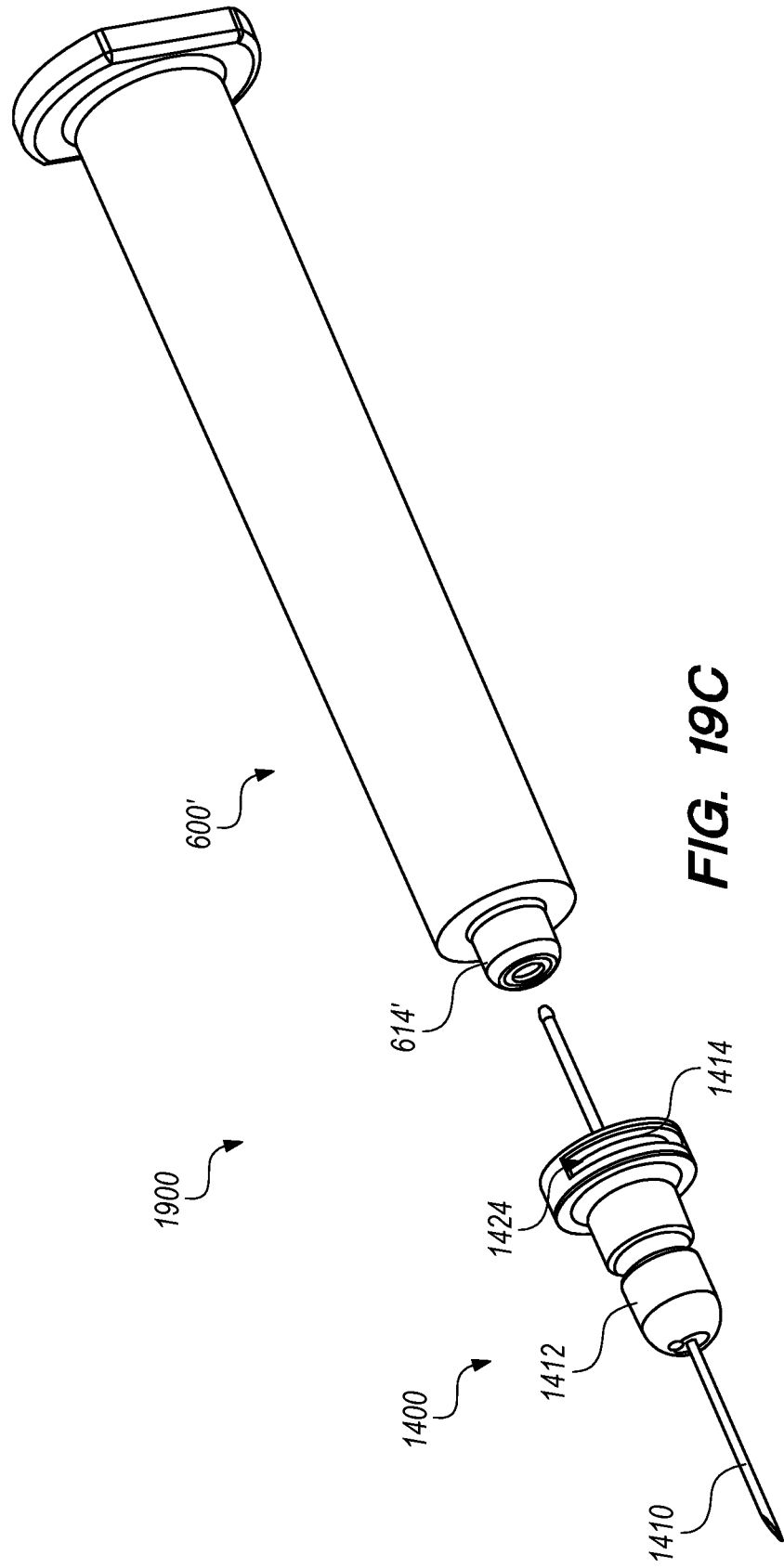
Figure 19D:
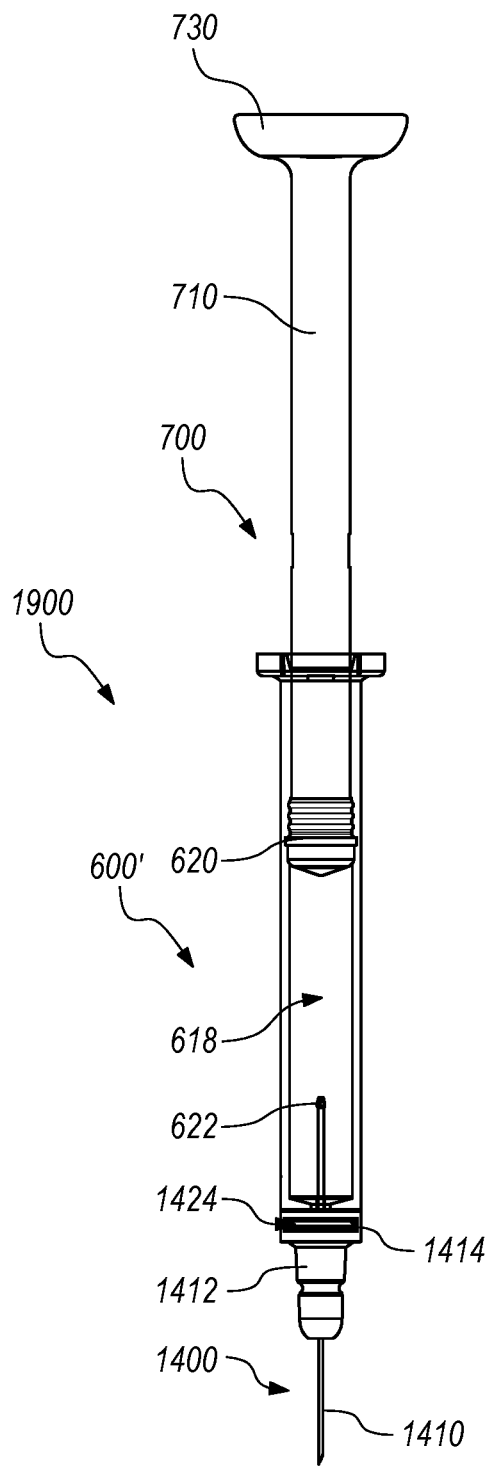
Figure 19E:
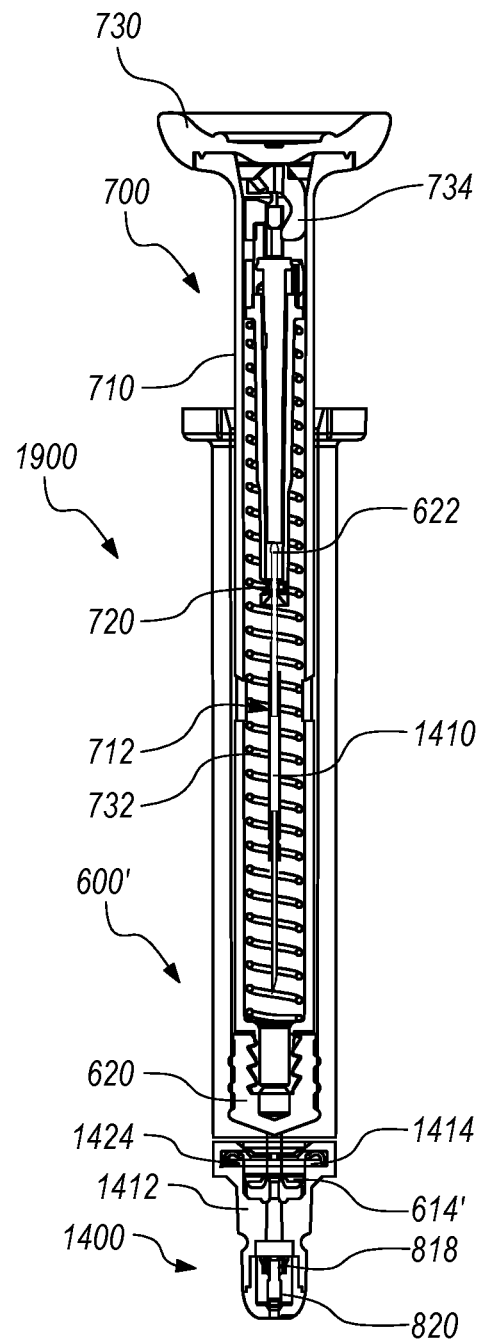

FIGS. 19C to 19E show perspective and side views of a safe injection system 1900 with a retaining ring 1414 according to some embodiments. The safe injection system 1900 facilitates injection of a medicine through a needle 1410 and retraction of the needle 1410 into the safe injection system 1900 such that a sharp distal end of the needle 1410 is contained therein to prevent accidental needle sticks.

The safe injection system 1900 includes a molded polymeric syringe body 600' defining a medicine chamber 618, a stopper member 620 occluding the proximal end of the medicine chamber 618, and a needle coupling member 614' formed at the distal end of the molded polymeric syringe body 600'. The medicine chamber 618 may have an inert coating on the interior surfaces thereof. The safe injection system 1900 also includes a plunger assembly 700. The plunger assembly 700 is coupled to the stopper member 620, and includes a plunger housing member 710 and a plunger manipulation interface 730.

Figure 15:
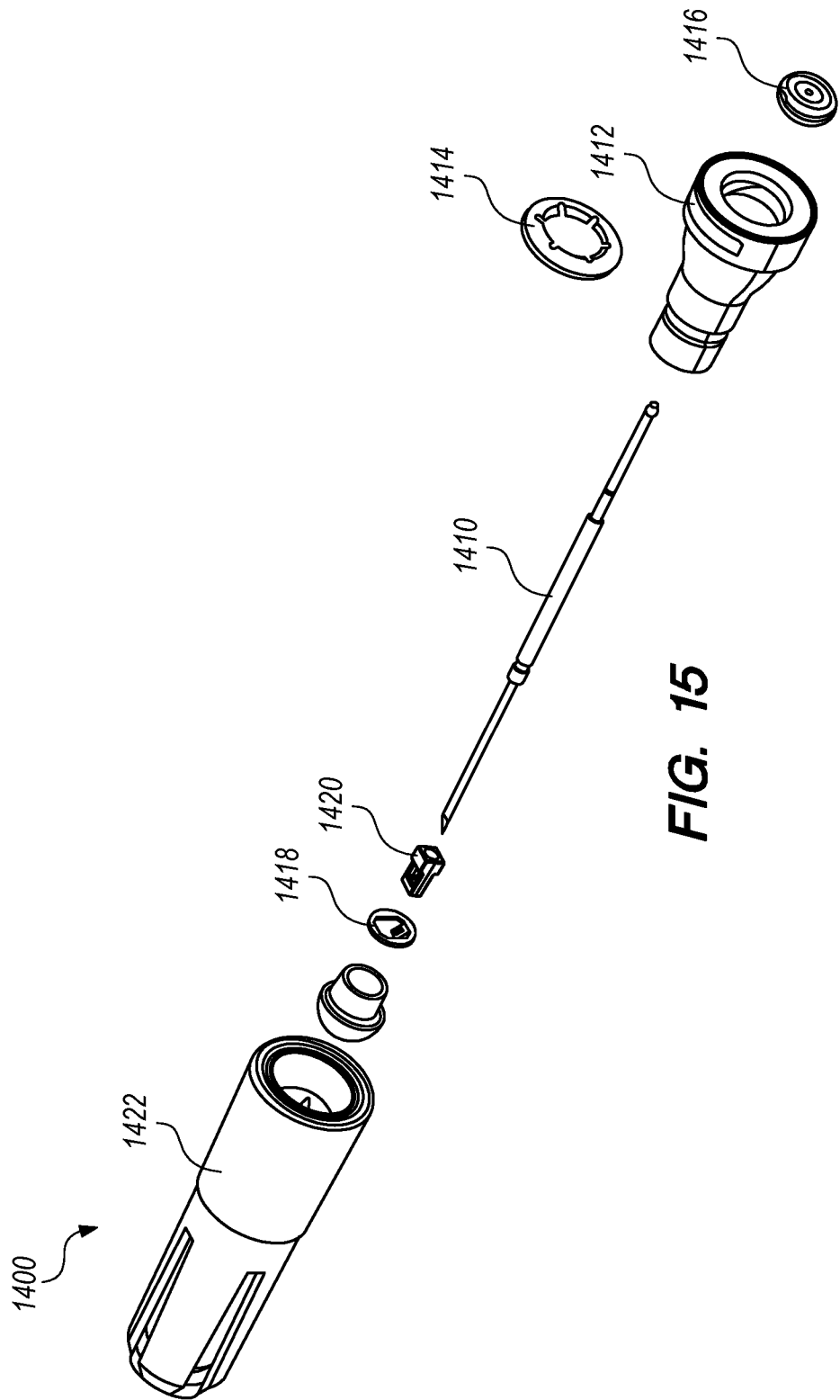

The safe injection system 1900 further includes a needle hub assembly 1400 having a needle 1410 releasable coupled to a needle hub 1412 by a needle latch 818 as shown in FIGS. 15 and 16B, and described above. As shown in FIGS. 15 and 16B and described above, the retaining ring 1414 allows the needle hub assembly 1400 to be inserted over the needle coupling member 614', but prevents removal of the needle hub assembly 1400 therefrom. The needle latch 818 prevents proximal movement of the needle 1410 relative to the needle hub 1412 until the needle latch 818 is opened/released by distal movement of the needle 1410. Distal movement of the needle 1410 (from force applied through the stopper member 620, the plunger housing member 710, and the plunger manipulation interface 730) causes distal movement of a needle latch actuator 820 to open/release the needle latch 818.

The safe injection system 1900 controls exit of medicine from the chamber 618 distally subject to insertion of the plunger assembly 700 relative to the syringe body 600' by a user. FIG. 19B shows the safe injection system 1900 in a pre-injection configuration. With application of distally directed force onto the plunger manipulation interface 730, the plunger member 700 is moved distally relative to the molded polymeric syringe body 600', thereby expelling medicine from the chamber 618 through the needle 1410 to perform an injection.

FIG. 19C shows the safe injection system 1900 in a post-injection, safe configuration. When the plunger member 700 has been manipulated distally such that the stopper member 620 is positioned near the distal end of the molded polymeric syringe body 600', a proximal end 622 of the needle 1410 pierces completely through the stopper member 620 and into a plunger interior 712 defined by the plunger housing member 710. After entering the plunger interior 712 the proximal end 622 of the needle 1410 is coupled to/captured by a needle retraction member 720 in the plunger assembly 700. The needle retraction member 720 is initially in a distal position (not shown) in the plunger interior 712. The needle retraction member 720 is coupled to a needle retraction spring 732. The needle retraction spring 732 is held in a compressed state by a spring latch 734, when the needle retraction member 720 is in the distal position. The needle retraction member 720, the needle retraction spring 732, and the spring latch 734 reside within the plunger interior 712.

When the stopper member 620 is positioned near the distal end of the molded polymeric syringe body 600', the needle pushes the needle latch actuator 820 distally to open/release the needle latch 818, thereby allowing proximal movement of the needle 810 relative to the needle hub assembly 800. When the stopper member 620 is reaches the distal end of the molded polymeric syringe body 600', the needle retraction member 720 actuates the spring latch 734, thereby releasing the needle retraction spring 732. Because the needle latch actuator 820 has already opened/released the needle latch 818, when the needle retraction member 720 actuates the spring latch 734, the needle retraction spring expands, thereby moving the needle retraction member 720 and the needle 810 coupled thereto into the plunger interior 712, as shown in FIG. 19C. The sharp distal tip of the needle 810 is retracted into the plunger interior 712 and the stopper member 620 to prevent accidental needle sticks after the injection is complete. In other embodiments, the sharp tip of the needle 1410 is retracted to a position proximal to the distal end of the needle hub 1412 to prevent inadvertent needle sticks. Additional details regarding exemplary safe needle retraction mechanism are described in U.S. patent application Ser. Nos. 14/696,342, 14/543,787, 14/321,706, 62/416,102, 62/431,382, and 62/480,276, the contents of which have been previously incorporated by reference herein.

Locking Detent and Braking Tab

Figure 20:
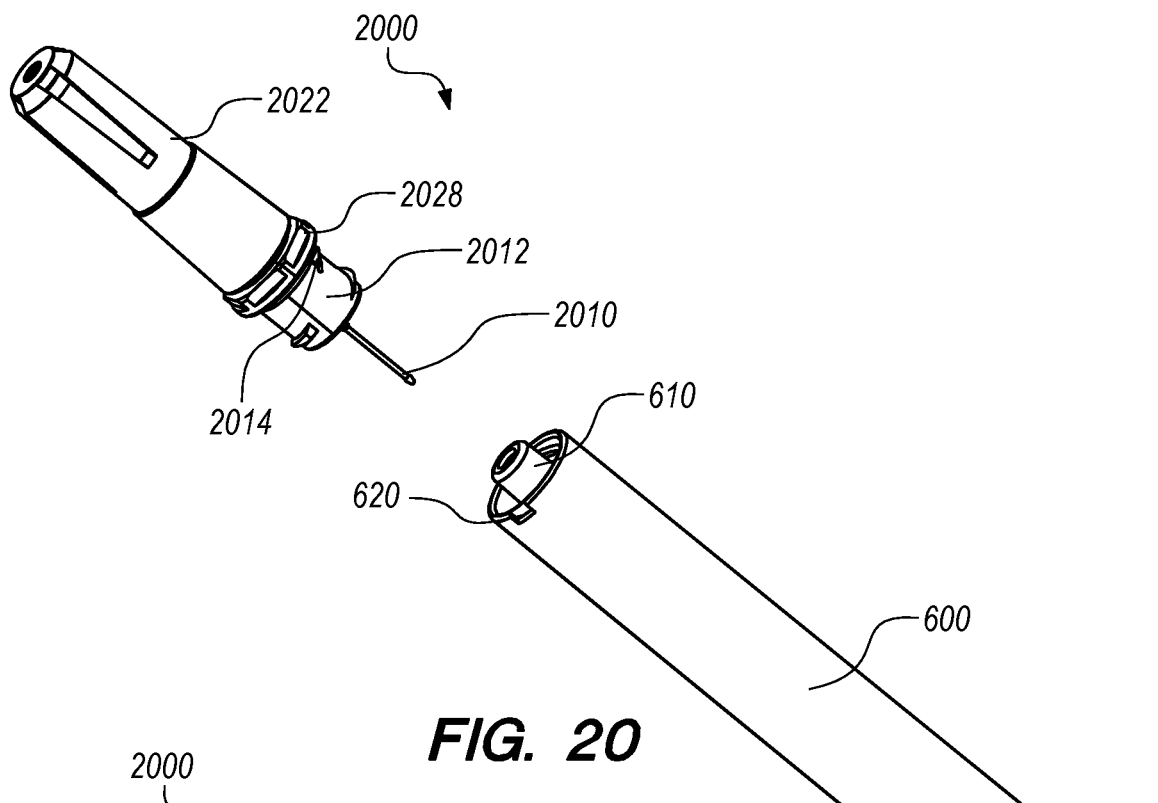
FIGS. 20 to 22 depict coupling of a needle hub assembly having a locking detent with a molded polymer injection system body having a corresponding notch according to some embodiments.
Figure 21:
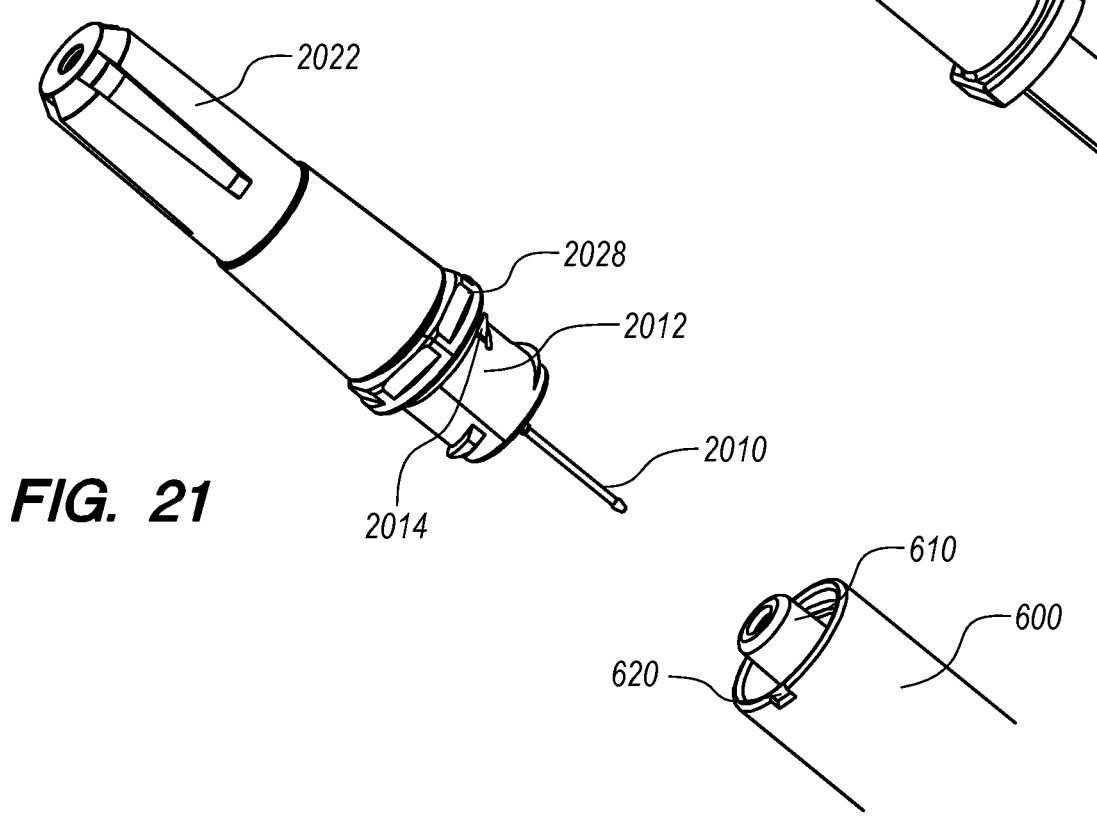
Figure 22:
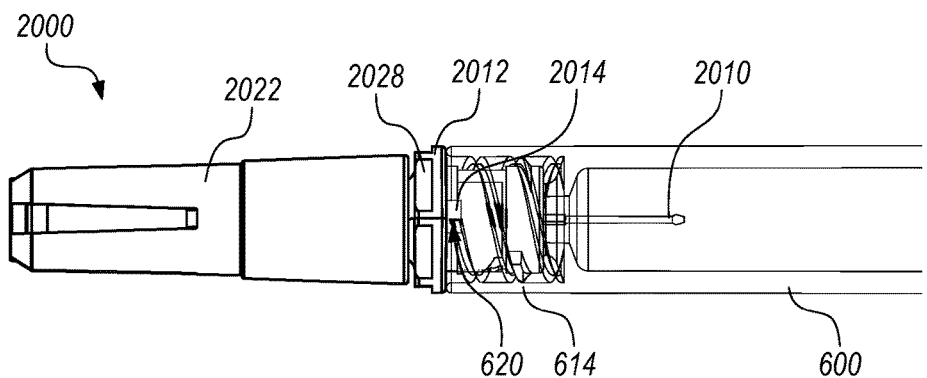

FIGS. 20 to 22 depict a needle hub assembly 2000 for use with molded polymer injection system bodies according to some embodiments. The needle hub assembly 2000 includes a needle 2010, a needle hub 2012 having a locking detent 2014, and a rigid needle shield 2022.

The detent 2014 extends from a proximally facing surface of the needle hub 2012. When the needle hub assembly 2000 is rotated clockwise onto the molded polymer syringe body 600, the detent 2014 slides into a notch 620 formed in the molded polymer syringe body 600. The slope of the detent 2014 allowed the detent 2014 to slide into the notch 620 with clockwise rotation, but prevents counterclockwise rotation. While clockwise rotation is allowed and counterclockwise rotation is prevented in this embodiment, other embodiments may allow counterclockwise rotation and prevents clockwise rotation by modifying the direction of the detent 2014 and the inwardly facing threads in the molded polymer injection system body. While the illustrations depict a single detent 2014 and notch 620, the system may include respective pluralities of detents and notches. While the notch is depicted in the distal surface of an integral molded syringe body 600, the notch may be formed in the distal surface of a molded polymer luer interface 614 which is attached to the distal end of a glass syringe.

The needle hub 2012 also includes a plurality of recesses 2028 with flat surfaces. The recesses 2028 on the needle hub 2012 allow a wrench or socket-like device (not shown) to rotate the needle hub assembly 2000 relative to the molded polymer syringe body 600. The wrench or socket-like device can be manipulated by a user or by a robot, thereby facilitating both manual and automated assembly.

FIGS. 23 to 28B depict a needle hub assembly 2300 for use with injection system bodies according to some embodiments. The needle hub assembly 2300 includes a needle 2310, a needle hub 2312 having a braking tab 2314, a needle latch 2318 (see FIG. 28A), and a needle latch actuator 2320 (see FIG. 28A).

Figure 7:
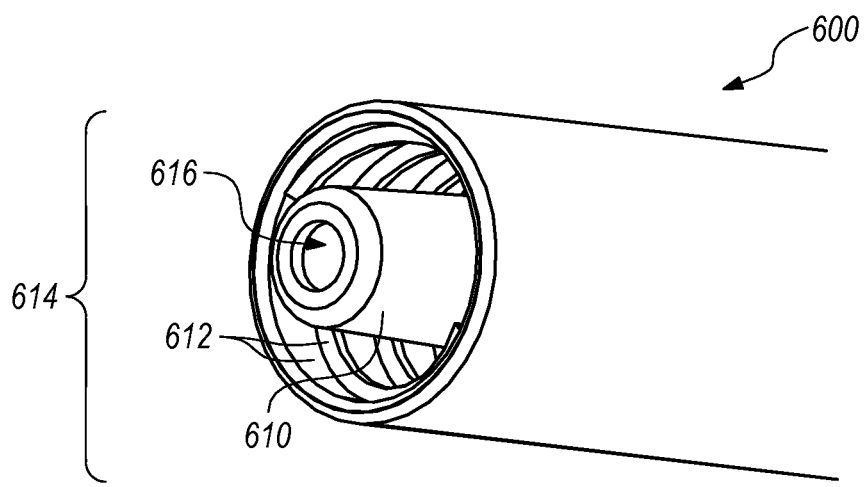
Figure 23:
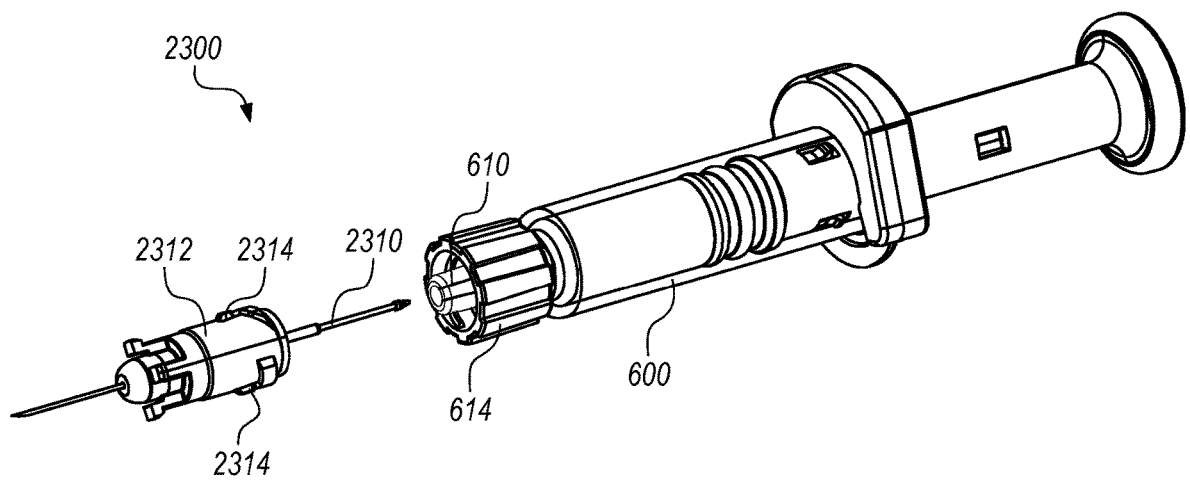
FIG. 23 depicts coupling of a needle hub assembly having a braking tab with a molded polymer injection system body according to some embodiments.
Figure 24A:
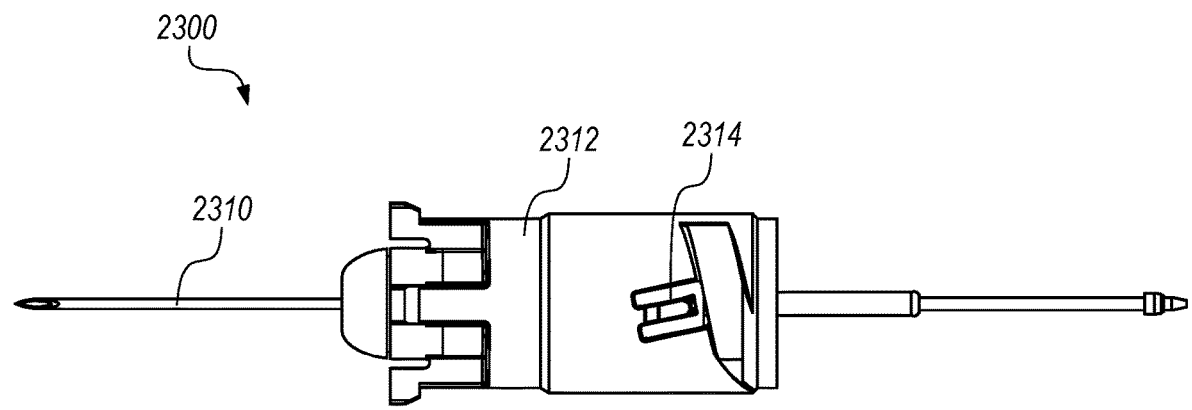
FIGS. 24A and 24B depict a needle hub assembly having a braking tab in two positions according to some embodiments.
Figure 24B:
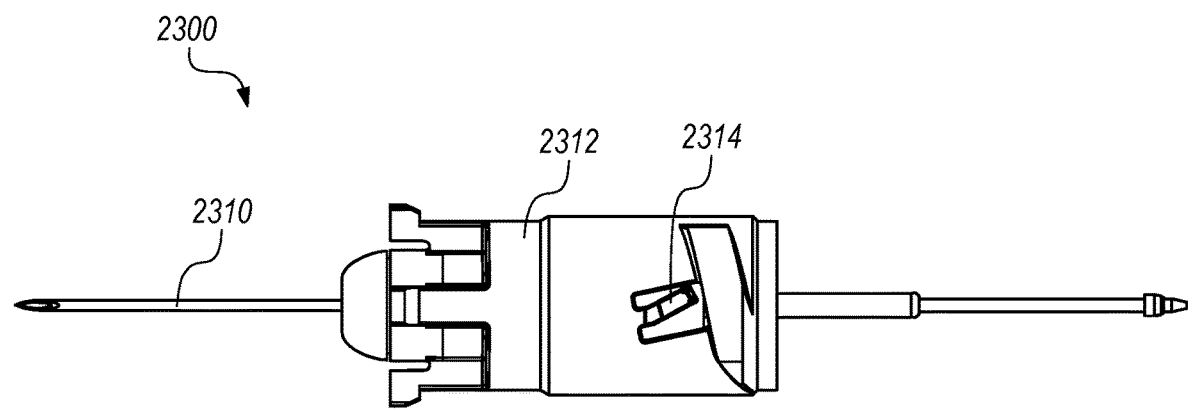
Figure 25:
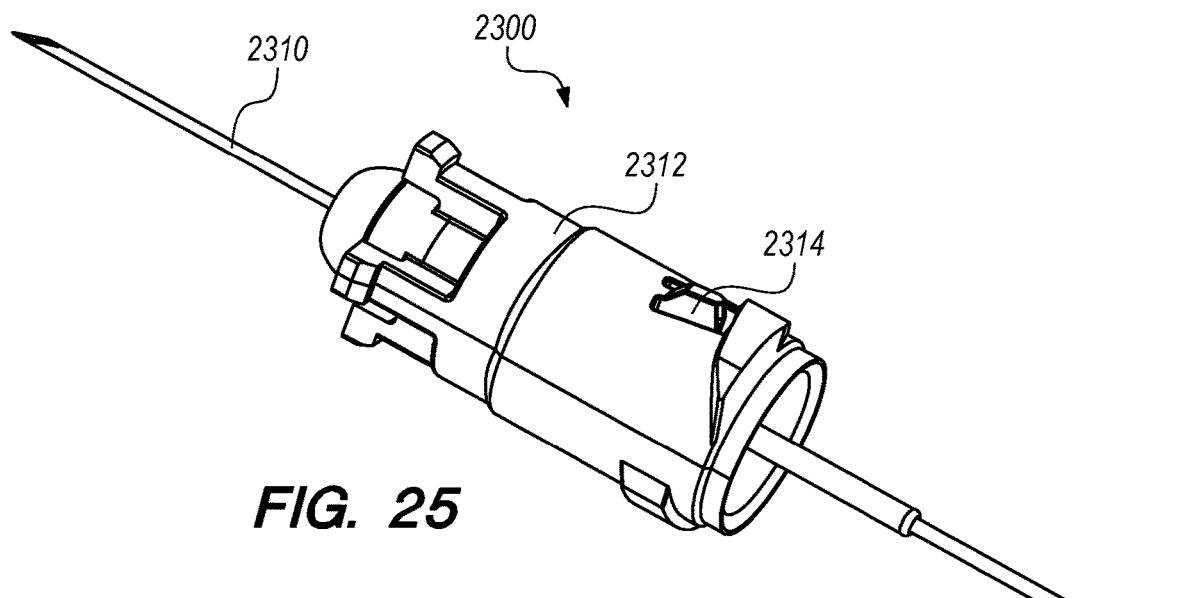
FIGS. 25 and 26 depict a needle hub assembly having a braking tab according to some embodiments.
Figure 26:
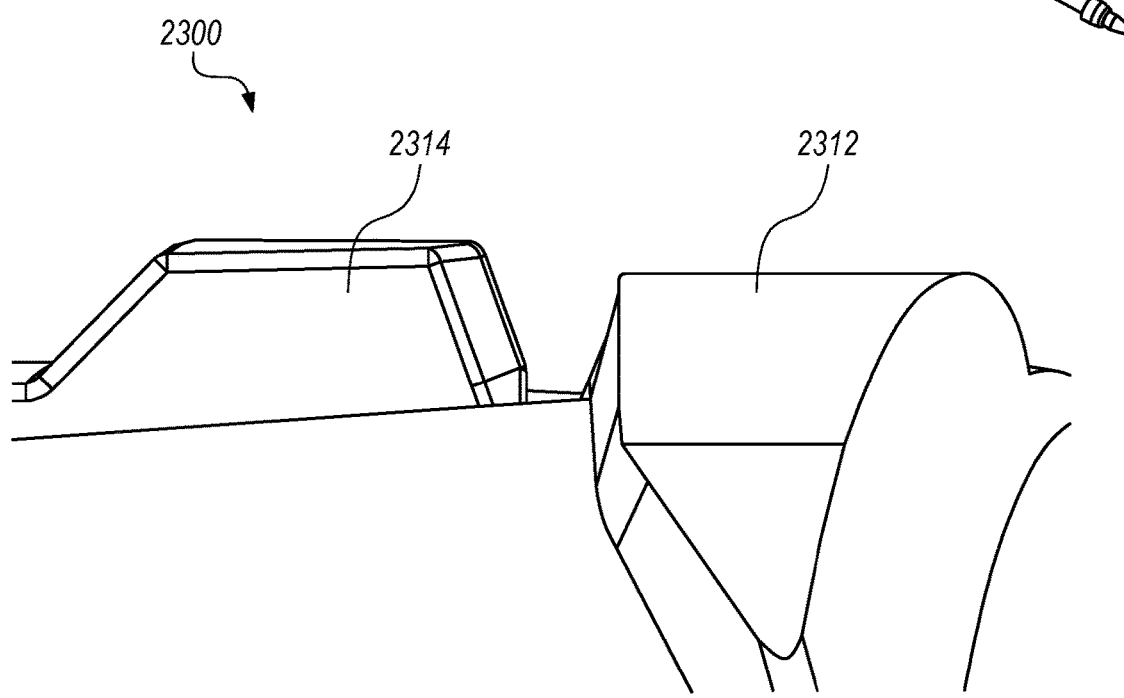

The injection system body 600 shown here is a glass syringe body 600 with an internally threaded needle coupling assembly/luer nut 614 attached to the distal end thereof. The braking tabs may also be used in a full integral polymer injection system body with an integral needle coupling assembly/luer nut as shown in FIG. 7 above. The braking tab 2314 is shown in detail in FIGS. 24A, 24B, 25, 26, and 28B. As shown in FIGS. 24A and 24B, the braking tab 2314 has to positions. FIG. 24A shows the braking tab 2314 in an unlocked position, which allows clockwise rotation of the needle hub 2312 relative to the injection system body 600 to couple the needle hub 2312 to the injection system body 600. FIG. 24B shows the braking tab 2314 in a locked position, which prevents counterclockwise rotation the needle hub 2312 relative to the injection system body 600 to remove the needle hub 2312 from the injection system body 600. Coupling the needle hub 2312 to the injection system body 600 by clockwise rotation transforms the braking tab 2314 from the unlocked position to the locked position. Therefore, the braking tab 2314 allows the needle hub assembly 2300 to be rotated clockwise onto the injection system body 600, but prevents counterclockwise rotation to remove the needle hub assembly 2300 from the injection system body 600. While a plurality of braking tabs 2314 is shown in FIG. 23, the injection system may be configured to use a single braking tab.

Figure 28A:
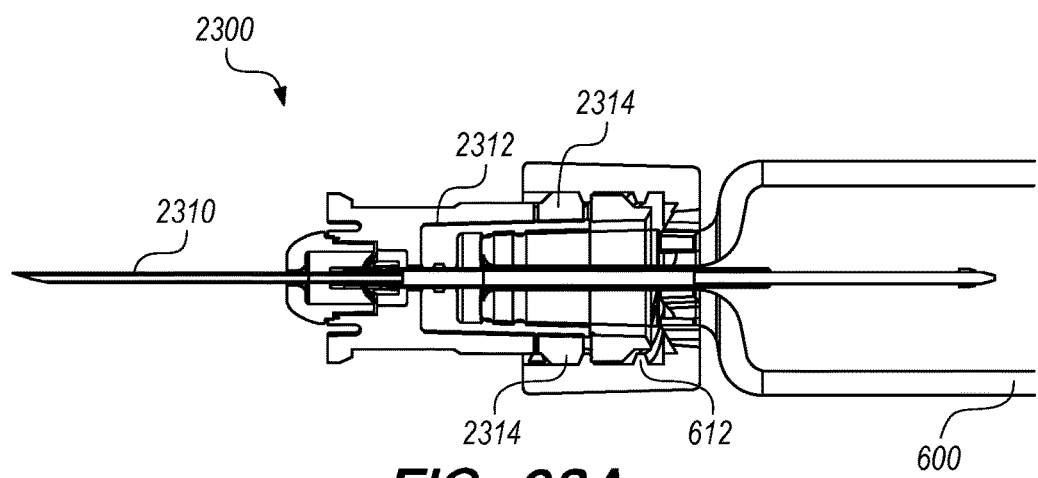
Figure 28B:
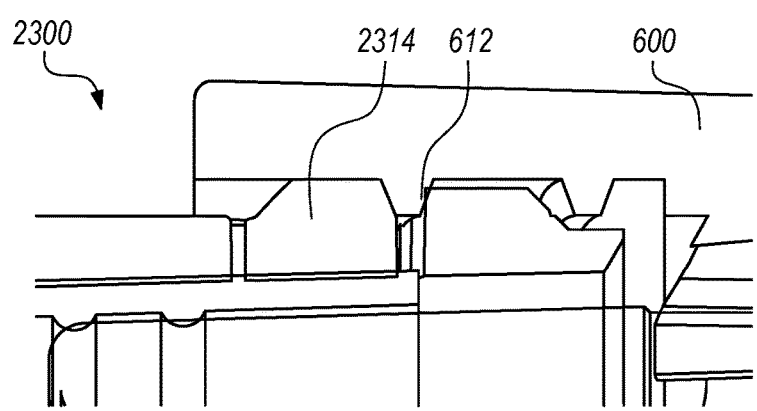

FIGS. 28A and 28B show that when the needle hub assembly 2300 is rotated clockwise onto the injection system body 600, the tab 2314 may expand due to pressure from the injection system body 600 and grip the inwardly facing threads on the injection system body 600. This further prevents counterclockwise rotation to remove the needle hub assembly 2300 from the injection system body 600. While clockwise rotation is allowed and counterclockwise rotation is prevented in this embodiment, other embodiments may allow counterclockwise rotation and prevents clockwise rotation by modifying the direction of the braking tab 2314 and the inwardly facing threads in the injection system body.

While the needle hub assemblies 2000, 2300 are shown without a seal/guide, in other embodiments, a seal/guide similar to those in needle hub assemblies 800, 1400 are present in the needle hub assemblies 2000, 2300. Such a seal/guide would seal an interior of the molded polymer injection system body 600 and center the needle/tube 2010 in the molded polymer injection system body 600. The injection system body may be a syringe body or a cartridge body. The injection system body 600 may have an inert coating on the interior surfaces thereof.

Exemplary Safe Syringe System (with Locking Detent or Braking Tab)

FIGS. 29A and 29B show side views of a safe injection system 2900 with a brake tab 2314 according to some embodiments. The safe injection system 2900 facilitates injection of a medicine through a needle 810 and retraction of the needle 810 into the safe injection system 2900 such that a sharp distal end of the needle is contained therein to prevent accidental needle sticks.

The safe injection system 2900 includes an injection system body 600" defining a medicine chamber 618, a stopper member 620 occluding the proximal end of the medicine chamber 618, and a needle coupling assembly 614 formed at the distal end of the injection system body 600". The safe injection system 2900 also includes a plunger assembly 700. The plunger assembly 700 is coupled to the stopper member 620, and includes a plunger housing member 710 and a plunger manipulation interface 730.

Figure 27:
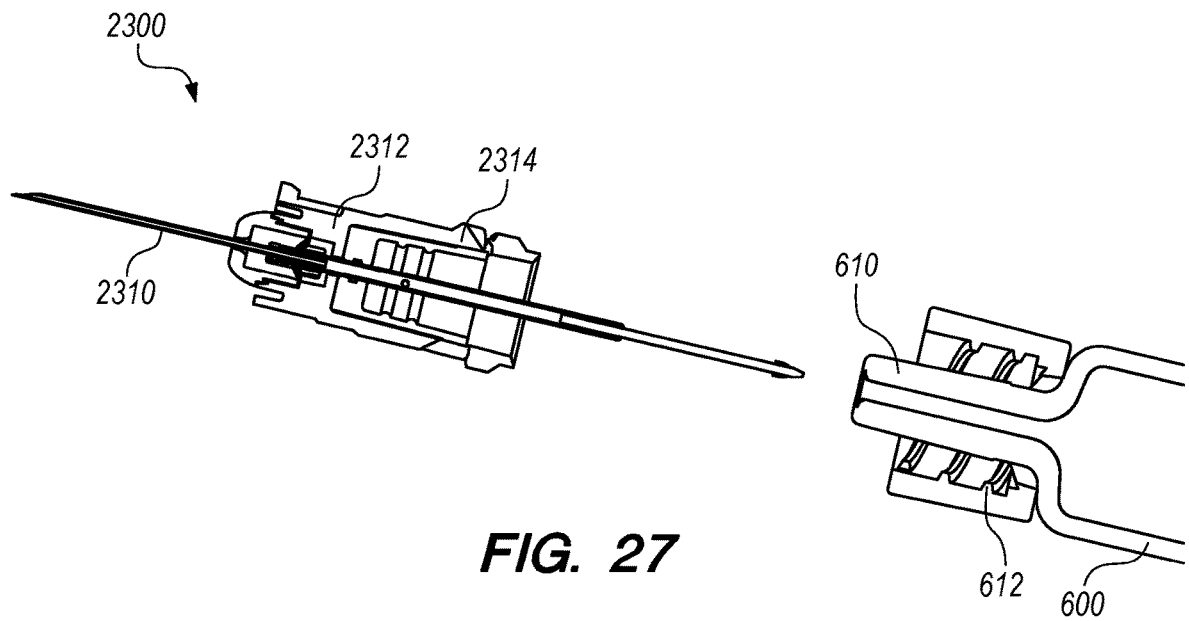
FIGS. 27 to 28B depicts coupling of a needle hub assembly having a braking tab with a molded polymer injection system body according to some embodiments.

The safe injection system 2900 further includes a needle hub assembly 2300 having a needle 2310 releasable coupled to a threaded needle hub 2312 by a needle latch 818 as described below. The threaded needle hub 2312 may be coupled to the needle coupling assembly 614 via the inwardly facing threads 612" on the needle coupling assembly 614. As shown in FIGS. 27 to 28B and described above, the brake tab 2314 allows the needle hub assembly 2300 to be threaded onto the needle coupling assembly 614, but prevents removal of the needle hub assembly 2300 therefrom. The needle latch 818 prevents proximal movement of the needle 2310 relative to the threaded needle hub 2312 until the needle latch 818 is opened/released by distal movement of the needle 2310. Distal movement of the needle 2310 (from force applied through the stopper member 620, the plunger housing member 710, and the plunger manipulation interface 730) causes distal movement of a needle latch actuator 820 to open/release the needle latch 818.

The safe injection system 2900 controls exit of medicine from the chamber 618 distally subject to insertion of the plunger assembly 700 relative to the injection system body 600″ by a user. FIG. 29A shows the safe injection system 2900 in a pre-injection configuration. With application of distally directed force onto the plunger manipulation interface 730, the plunger member 700 is moved distally relative to the molded polymeric injection system body 600″, thereby expelling medicine from the chamber 618 through the needle 2310 to perform an injection.

FIG. 29B shows the safe injection system 2900 in a post-injection, safe configuration. When the plunger member 700 has been manipulated distally such that the stopper member 620 is positioned near the distal end of the molded polymeric injection system body 600″, a proximal end 622 of the needle 2310 pierces completely through the stopper member 620 and into a plunger interior 712 defined by the plunger housing member 710. After entering the plunger interior 712 the proximal end 622 of the needle 2310 is coupled to/captured by a needle retraction member 720 in the plunger assembly 700. The needle retraction member 720 is initially in a distal position (not shown) in the plunger interior 712. The needle retraction member 720 is coupled to a needle retraction spring 732. The needle retraction spring 732 is held in a compressed state by a spring latch 734, when the needle retraction member 720 is in the distal position. The needle retraction member 720, the needle retraction spring 732, and the spring latch 734 reside within the plunger interior 712.

When the stopper member 620 is positioned near the distal end of the injection system body 600″, the needle pushes the needle latch actuator 820 distally to open/release the needle latch 818, thereby allowing proximal movement of the needle 2310 relative to the needle hub assembly 2300. When the stopper member 620 is reaches the distal end of the molded polymeric injection system body 600″, the needle retraction member 720 actuates the spring latch 734, thereby releasing the needle retraction spring 732. Because the needle latch actuator 820 has already opened/released the needle latch 818, when the needle retraction member 720 actuates the spring latch 734, the needle retraction spring expands, thereby moving the needle retraction member 720 and the needle 2310 coupled thereto into the plunger interior 712, as shown in FIG. 29B. The sharp distal tip of the needle 2310 is retracted to a position proximal to the distal end of the threaded needle hub 2312 to prevent accidental needle sticks after the injection is complete. At least one portion of the needle 2310 is retracted at least partially through the stopper member 620. In other embodiments, the sharp distal tip of the needle 2312 is retracted into the plunger interior 712 through the stopper member 620 to prevent accidental needle sticks. Additional details regarding exemplary safe needle retraction mechanism are described in U.S. patent application Ser. Nos. 14/696,342, 14/543,787, 14/321,706, 62/416,102, 62/431,382, and 62/480,276, the contents of which have been previously Incorporated by reference herein.

While FIGS. 29A and 29B depict a safe injection system 2900 with a brake tab 2314 according to some embodiments, a safe injection system with a locking detent 2014 would function in a manner similar to the safe injection system 2900 depicted in FIGS. 29A and 29B.

Additional Aspects

In addition to the claimed invention and by way of non-limiting examples, further embodiments or aspects of the invention are described herein.

1. An injection system, comprising:
   a molded body member comprising
   a body connection member at a distal end thereof, and
   a notch disposed on a distally facing surface thereof; and
   a needle hub assembly coupled to the distal end of the injection system body, the needle hub assembly comprising
   a needle hub coupled to the body connection member,
   a needle coupled to the needle hub, and
   a detent disposed on a proximally facing surface of the needle hub,
   wherein the detent is configured to fit in the notch and prevent preventing rotation of the needle hub assembly relative to the body connection member when the needle hub assembly is coupled to the body member.

2. The system of aspect 1, further comprising a stopper member disposed in the molded body member and a plunger member coupled thereto, wherein the needle is configured to be retracted at least partially into the molded body member upon manipulation of the plunger member to position the stopper member at the distal end of the molded body member.

3. The system of aspect 1, wherein the needle hub includes a plurality of recesses configured to facilitate rotation of the needle hub assembly relative to the body connection member.

4. The system of aspect 1, wherein the body connection member comprises a space having inward facing threads.

5. The system of aspect 1, wherein the body connection member comprises an integrated luer nut.

6. The system of aspect 1, further comprising a sealing member disposed between the distal end of the body member and an inner surface of the needle hub.

7. The system of aspect 6, wherein the sealing member comprises an inward extension configured to center the needle in the distal end of the body member.

8. The system of aspect 1, wherein the body member is molded from Cyclic Olefin Copolymer or Cyclic Olefin Polymer.

The anti-removal mechanisms disclosed herein prevent removal of the needle hub assembly from the injection system body both manually by the user and resulting from increased pressure in the injection system body during injection of the medicine through the needle. In particular, the anti-removal mechanisms disclosed herein prevent the pressure built up in the injection system body during injection from unthreading the needle hub assembly from the injection system body.

While the embodiments herein depict a molded polymer syringe body, the mechanisms for preventing removal of a needle hub assembly from a molded body member can also be used with molded polymer cartridges according to various embodiments.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject injection information collection procedures may be provided in packaged combination for use in executing such interventions. These supply "kits" may further include instructions for use and/or may be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. An injection system, comprising:
    a molded polymer body member having a body connection member at a distal end of the molded polymer body member; and
    a needle hub assembly coupled to the distal end of the molded polymer body member, the needle hub assembly comprising:
        a needle hub coupled to the body connection member of the molded polymer body member,
        a needle coupled to the needle hub, and
        a separately formed metal barbed band coupled to and disposed around a proximal end of the needle hub, the metal barbed band having:
            an integrally formed barb, and
            an integrally formed longitudinal extension configured to be received in an opening in the needle hub to prevent relative rotation of the metal barbed band and the needle hub,
    wherein the metal barbed band allows rotation of the needle hub assembly relative to the body connection member in a first direction, while preventing rotation of the needle hub assembly relative to the body connection member in a second direction by the barb digging into the molded polymer body member.

2. The system of claim 1, further comprising a stopper member disposed in the molded polymer body member and a plunger member coupled to the stopper member, wherein the needle is configured to be retracted at least partially into the molded polymer body member upon manipulation of the plunger member to position the stopper member at the distal end of the molded polymer body member.

3. The system of claim 1, wherein the needle hub includes a plurality of recesses configured to facilitate the rotation of the needle hub assembly relative to the body connection member.

4. The system of claim 1, wherein the body connection member comprises a space having inward facing threads.

5. The system of claim 1, wherein the body connection member comprises an integrated luer nut.

6. The system of claim 1, further comprising a sealing member disposed between the distal end of the molded polymer body member and an inner surface of the needle hub.

7. The system of claim 6, wherein the sealing member comprises an inward extension configured to center the needle in the distal end of the molded polymer body member.

8. The system of claim 7, wherein the inward extension of the sealing member comprises a plurality of extensions.

9. The system of claim 1, wherein the molded polymer body member is molded from Cyclic Olefin Copolymer or Cyclic Olefin Polymer.

10. The system of claim 1, wherein the barb comprises a plurality of barbs.

* * * * *